(12) United States Patent
Kastan et al.

(10) Patent No.: US 6,348,311 B1
(45) Date of Patent: Feb. 19, 2002

(54) ATM KINASE MODULATION FOR SCREENING AND THERAPIES

(75) Inventors: Michael Kastan; Christine Canman; Seong-Tae Kim; Dae-Sik Lim, all of Cordova, TN (US)

(73) Assignees: St. Jude Childre's Research Hospital, Memphis, TN (US); Johns-Hopkins University, Baltimore, MD (US)

( * ) Notice: Subject to any disclaimer, the term of this patent is extended or adjusted under 35 U.S.C. 154(b) by 0 days.

(21) Appl. No.: 09/400,653

(22) Filed: Sep. 21, 1999

Related U.S. Application Data

(63) Continuation of application No. 09/248,061, filed on Feb. 10, 1999.

(51) Int. Cl.[7] .............................. C12Q 1/70; C12Q 1/48
(52) U.S. Cl. ............................................. 435/5; 435/15
(58) Field of Search ........................................ 435/15, 5

(56) References Cited

U.S. PATENT DOCUMENTS

| | | | |
|---|---|---|---|
| 5,728,807 A | 3/1998 | Shiloh et al. | 530/350 |
| 5,756,288 A | 5/1998 | Shiloh | 435/6 |
| 5,777,093 A | 7/1998 | Shiloh et al. | 536/235 |

FOREIGN PATENT DOCUMENTS

| | | |
|---|---|---|
| GB | 2327498 | 1/1999 |
| WO | 97/18323 | 5/1997 |
| WO | 98/55602 | 12/1998 |
| WO | 98/56391 | 12/1998 |

OTHER PUBLICATIONS

Salles–Passadore et al., *Life Sciences,* 322:113–120, 1999.
Canman et al., *Science* 281:1677, 1998.
Cliby et al., *EMBO J,* 17:159, 1998.
Baskaran et al., *Nature,* 387:516, 1997.
Morgan et al., *Mol. Cell Biol,* 17:2020, 1997.
Morgan and Kastan, *Adv. Cancer Res.,* 71:1, 1997.
Kastan, *New Eng. J. Med.* 333:662, 1995.
Canman et al., *Cancer Res.,* 54:5054, 1994.
Hartwell and Kastan, *Science,* 266:1821, 1994.
Nelson et al., *Mol. Cell Biol.,* 14:1815, 1994.
Kastan et al., *Cell,* 71:587, 1992.
Banin et al., *Science,* 281:1674–1677, 1998.
Flaggs et al., *Current Biology,* 7(12):977–986, 1997.
Kim et al., *Journal of Biological Chemistry,* 274(53):37538–37543, 1999.
Sanchez et al., *Science,* 277:1497–1501, 1997.
Scott et al., *Biochemical and Biophysical Research Communications,* 245:144–148, 1998.

*Primary Examiner*—Rebecca E. Prouty
*Assistant Examiner*—Maryam Monshipouri
(74) *Attorney, Agent, or Firm*—Darby & Darby

(57) ABSTRACT

The present invention relates to identification of the consensus sequence phosphorylated by ATM kinase. This, in turn, permitted identification of ATM kinase target proteins, and development of a convenient assay system for ATM kinase phosphorylation using fusion polypeptides as substrates. The assay system is adaptable to screening for ATM modulators, particularly inhibitors. In a specific embodiment, the substrate recognition sequence and mutagenized variants of this sequence were incorporated in a GST fusion protein and assayed for phosphorylation by ATM kinase. This assay system is useful in screening for ATM inhibitors. ATM function assays were validated using an ATM-kinase dead dominant-negative mutant.

2 Claims, 4 Drawing Sheets

ATM KINASE MODULATION FOR SCREENING AND THERAPIES

This application is a continuation in part of U.S. application No. 09/248, 061 filed 02/10/1999 pending.

The research leading to the present invention was supported, in part, by National Institute of Health grants CA71387 and ES05777. Accordingly, the Government has certain rights in the invention.

FIELD OF THE INVENTION

The present invention relates to identification of the consensus sequence phosphorylated by ATM kinase. This, in turn, permitted identification of ATM kinase target proteins, and development of a convenient assay system for ATM kinase phosphorylation using fusion polypeptides as substrates. The assay system is adaptable to screening for ATM modulators, particularly inhibitors.

BACKGROUND OF THE INVENTION

Ataxia telangiectasia (AT) is a rare autosomal recessive multi-system disorder characterized by clinical manifestations that include progressive cerebellar ataxia, neuronal degeneration, hypersensitivity to ionizing irradiation (IR), premature aging, hypogonadism, growth retardation, immune deficiency, and an increased risk for cancer (Lavin and Shiloh, Annu. Rev. Immunol., 15:177, 1997). Cancer predisposition in AT is striking: 38% of patients develop malignancies, mainly lymphoreticular neoplasms and leukemias. But AT patients manifest acute radiosensitivity and must be treated with reduced radiation doses, and not with radiomimetic chemotherapy. AT has a worldwide frequency of 1:100,000 live births and an estimated carrier frequency of 1% in the American population. Notable concentrations of AT patients outside the United States are in Turkey, Italy, and Israel.

Cerebellar ataxia that gradually develops into general motor dysfunction is the first clinical hallmark and results from progressive loss of Purkinje cells in the cerebellum. Oculocutaneous telangiectasia (dilation of blood vessels) develops in the bulbar conjunctiva and facial skin, and is later accompanied by graying of the hair and atrophic changes in the skin. Somatic growth is retarded in most patients, and ovarian dysgenesis is typical for female patients. Among occasional endocrine abnormalities, insulin-resistant diabetes is predominant, and serum levels of alpha-fetoprotein and carcinoembryonic antigen are elevated. The thymus is either absent or vestigial, and other immunological defects include reduced levels of serum IgA, IgE or IgG2, peripheral lymphopenia, and reduced responses to viral antigens and allogeneic cells. These immunological defects cause many patients to suffer from recurrent sinopulmonary infections. The most common cause of death in AT, typically during the second or third decade of life, is from these sinopulmonary infections with or without malignancy.

The gene mutated in AT, ATM (Ataxia Telangiectasia-Mutated), encodes a 370-kD protein that is a member of a family of proteins related to phosphatidylinositol 3-kinase (PI-3-K) that have either lipid or protein kinase activity. A subset of this family with the greatest homology to ATM functions in DNA repair, DNA recombination, and cell cycle control (Savitsky et al., Science, 268:1749, 1995; Keith and Screiber, ibid., 270:50, 1995). Cell lines derived from AT patients exhibit hypersensitivity to ionizing radiation (IR) and defects in several IR-inducible cell cycle checkpoints, including a diminished irradiation-induced arrest in the G1 phase of the cell cycle mediated by the p53 tumor suppressor gene product (Kastan et al., Cell, 71:587, 1992; Morgan and Kastan, Adv. Cancer Res., 71:1, 1997). In response to DNA damage, cells with wild type ATM accumulate p53 protein and show a subsequent increase in p53 activity, whereas cells with defective ATM show a smaller increase in the amount of p53 protein in response to IR (Kastan et al., supra; Canman et al., Cancer Res., 54:5054, 1994; Khanna and Lavin, Oncogene, 8:3307, 1993). Therefore, ATM appears to act upstream of p53 in a signal transduction pathway initiated by IR.

p95/nibrin has recently been shown to be the gene mutated in the Nijmegen breakage syndrome (NBS), which is an autosomal recessive disease with a phenotype (radiation sensitivity, predisposition to malignancies, and chromosomal instability) virtually identical to that of AT (Shiloh, 1997; Carney et al., 1998; Varon et al., 1998; Featherstone and Jackson, 1998). The main distinction between the AT and NBS syndromes is that AT patients exhibit progressive ataxia while NBS patients have microcephaly as their neurologic abnormality. p95/nibrin is part of a double-strand break DNA repair protein complex containing Rad50 and MRE11 (Carney et al., 1998; Dong et al., 1999; Paul and Gellert, 1999). The overlapping phenotypes of AT and NBS suggest that ATM and p95/nibrin may play a role in the same cellular pathways, likely including roles in responses to DNA damage. Identifying p95/nibrin as an in vitro ATM kinase target led us to investigate potential in vivo interactions between p95/nibrin and ATM. We found that ATM protein can bind to p95/nibrin and that ATM activity is required for phosphorylation of p95 on Ser343 after IR. Thus, characterization of the ATM kinase and elucidation of in vitro targets led to identification of one valid physiologically significant target and will likely lead to further insights into ATM function and AT biology.

IR induces rapid, de novo phosphorylation of endogenous p53 at two serine residues within the first 24 amino acids of the protein, one of which was identified as $Ser^{15}$ (Shieh et el., Cell, 91:325, 1997; Siliciano et al., Genes Dev., 11:3471, 1997). Phosphorylation of p53 at $Ser^{15}$ in response to DNA damage correlates with both the accumulation of total p53 protein as well as with the ability of p53 to transactivate downstream target genes in wild type cells (Siliciano et al., supra). Furthermore, phosphorylation of p53 on $Ser^{15}$ in response to IR is diminished in cell lines derived from AT patients, suggesting that ATM participates in this response (Siliciano et al., supra).

The PI3-K-related protein, DNA-activated protein kinase (DNA-PK), phosphorylates p53 in vitro at two different SQ motifs, $Ser^{15}$ and $Ser^{37}$ (Lees-Miller et al., Mol. Cell Biol., 12:5041, 1992). However, cells with diminished DNA-PK activity still normally accumulate p53 protein and undergo G1 arrest in response to IR (Rathmell et al., Cancer Res., 57:68, 1997; Guialos et al., Genes Dev., 10:2038, 1996; Nacht et al., ibid., p. 2055).

The concept of inhibiting ATM for the treatment of neoplasms, particularly cancers associated with decreased p53 function, has been suggested (Morgan et al., Mol. Cell Biol. 17:2020, 1997; Hartwell and Kastan, Science, 266:1821, 1994; Kastan, New Eng. J. Med. 333:662, 1995; see also WO 98/56391, Westphal and Leder). In particular, Westphal and Leder provide genetically manipulated knockout mice as a model for testing ATM inhibitors. This published application suggests using an inhibitory antibody to ATM, a dominant negative fragment of ATM (see also Morgan et al., Supra), or an ATM antisense strategy to inhibit ATM. However, while these publications propose inhibiting ATM to enhance radiosensitivity of neoplastic cells, and screening for compounds that inhibit ATM activity, they provide no specific screening test, particularly one suitable for high through-put screening. There is no hint or suggestion in these publications of strategies for targeting the kinase activity of ATM, the nature of an ATM kinase substrate recognition sequence, or of sequences recognized specifically by ATM, but not other kinases. There is also no information about the function of other ATM target proteins besides p53.

Accordingly, there is a need in the art to understand ATM kinase specificity. There is a further need to identify ATM target proteins other than p53.

These and other needs in the art are addressed by the present invention.

SUMMARY OF THE INVENTION

The present invention relates to the identification of an ATM kinase substrate recognition consensus sequence motif, and to the identification of new ATM target proteins, which in turn has led to the discovery of unexpected and novel ATM-regulated cellular pathways.

Thus, in one embodiment, the invention advantageously provides a method for identifying an ATM kinase substrate recognition sequence in a protein. This method comprises contacting an ATM kinase with a fusion polypeptide and detecting whether binding has occurred between the ATM kinase and the fusion polypeptide. The fusion polypeptide contains a structural portion and a candidate ATM-kinase substrate recognition sequence portion. Moreover, given application of sequence comparison techniques, the invention provides a method for identifying a putative ATM target protein, by analyzing the sequence of the protein to determine whether it contains an ATM substrate recognition consensus sequence motif.

In a further embodiment, a method for identifying an ATM-regulated pathway is provided. This method comprises identifying a substrate of an ATM kinase, e.g., as described above; modulating ATM-mediated phosphorylation of the target protein comprising an ATM recognition sequence; and determining whether modulation of ATM-mediated phosphorylation of the target protein affects a cellular pathway, which would indicate that the pathway is an ATM-regulated pathway. As a corollary, the invention provides a method for modulating an ATM-regulated pathway, which comprises modulating ATM-mediated phosphorylation of a target protein comprising an ATM-kinase recognition sequence in a cell.

The methods of the invention can involve a kinase-dead ATM mutant polypeptide. Thus, in a further embodiment, the invention provides a nucleic acid encoding such a polypeptide, as well as the polypeptide itself. The invention provides a recombinant vector which codes for expression of a defective ATM polypeptide, e.g., a kinase dead mutant, and a cell line containing such a vector.

In another embodiment, particularly in connection with methods for identifying an ATM kinase substrate recognition sequence and for screening, the invention provides a fusion polypeptide, wherein the fusion polypeptide contains a structural portion and an ATM-kinase recognition sequence portion.

In still another embodiment, the invention provides a method for screening for a compound that modulates ATM-mediated phosphorylation. This method comprises detecting whether there is a change in the level of ATM-mediated phosphorylation of a polypeptide comprising an ATM substrate recognition sequence in the presence of a candidate compound, wherein an increase in the level of phosphorylation indicates that the compound agonizes ATM-mediated phosphorylation, and a decrease in the level of phosphorylation indicates that the compound antagonizes ATM-mediated phosphorylation.

The invention further provides for screening for a compound that induces an ATM-regulated pathway in a cell, comprising contacting the cell with a candidate compound, and detecting whether the ATM-mediated pathway is induced in the cell, wherein the cell is defective for expression of ATM. In one embodiment, the screening can be for ATM-regulated cellular pathway, with the proviso that the pathway does not involve p53 or cell cycle control, or both.

The invention also provides methods for modulating ATM kinase activity in cells in vitro and in vivo. Such modulation includes inhibition of ATM kinase. In vivo modulation provides for evaluation of ATM function, e.g., in animal models. Alternatively, in vivo modulation of ATM function has therapeutic effects. In particular, ATM inhibition can enhance radiosensitivity and chemotherapeutic sensitivity in tumors, inhibit cell proliferation and induce revascularization in restenosis, and promote insulin signaling and increased metabolism in obesity.

In yet another embodiment, the invention provides a composition comprising ATM and a polypeptide, in which the polypeptide comprises an ATM kinase substrate recognition sequence, e.g., for co-crystallization or other methods of structure-function analysis. The results of such structural studies permit rational drug design and development.

These and other aspects of the present invention are further elaborated in the Detailed Description of the Invention and Examples, infra.

Figure 1A:
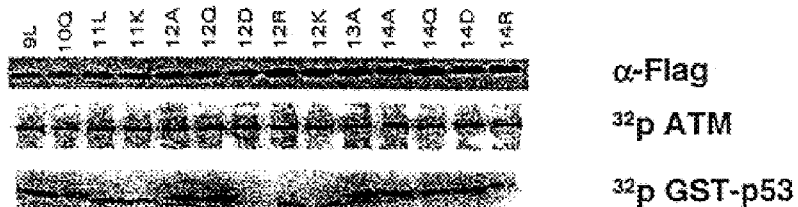
FIGS. 1A, 1B, and 1C. Phosphorylation of GST-p53 mutant peptides (amino acids 9–21) by ATM, ATR, and DNA-PK in vitro. In vitro kinase assays with immunoprecipitated, transfected flag-tagged ATM (A) or ATR (B) or purified DNA-PK (C) were performed with GST-p53 peptides containing the amino acid substitutions indicated. The amount of 32P-labeled GST-peptides was quantitated with a PhosphorImager and was normalized for each of the kinases to the level of phosphorylation of wild-type GST-p53.

Gy IR as indicated. The expression of Flag-ATM in each cell lysates was detected with anti-Flag antibody (top panel). Immunoprecipitated Myc-p95 was blotted with anti-a-p95-phosphoserine 343 antibody (middle panel) or anti-Myc antibody (lower panel). (B) Phosphorylation of endogenous p95 on Ser343 in normal cells, but not AT cells, after IR. Normal (WT, GM0536) or AT (GM1526) lymphoblasts were treated with either 0 (−) or 5 (+) Gy IR. Endogenous p95 was immunoprecipitated and blotted with anti-a-p95-phosphoserine 343 antibody (top panel) or anti-p95 antibody (lower panel).

DETAILED DESCRIPTION OF THE INVENTION

The present invention is based, in part, on the discovery of substrate recognition sequences of ATM kinase target proteins. The initial discovery was made using p53 as the target protein. Utilizing site-directed mutagenesis, the kinase recognition sequence in p53 was dissected, and the critical residues identified. Additional putative ATM kinase recognition sites were identified in other proteins, and these sequences were tested in a fusion polypeptide assay for the ability to be phosphorylated by ATM kinase. Using a reiterative process, a consensus sequence motif, termed herein an ATM kinase substrate recognition consensus sequence motif, has been determined.

In addition, kinase specificity has been evaluated, and distinctions between different kinases (ATM, DNA-PK, and ATR) have been found.

Coincident with characterization of the recognition consensus sequence motif, an assay for kinase activity was developed. In the present invention, a full-length ATM protein is expressed and used in phosphorylation assays, in which the presence of manganese has been found to be essential. Furthermore, a dominant-negative ATM kinase mutant was developed as a negative control for the assay. The assay used to characterize the ATM kinase substrate recognition consensus sequence motif further involves creating chimeric polypeptides comprising a putative ATM kinase substrate recognition sequence, which can be tested as phosphorylation substrates for the full-length ATM. The assay can be adapted for a number of purposes.

First, putative ATM kinase recognition sites from possible target proteins can be inserted in the ATM kinase substrate polypeptide and tested for phosphorylation by ATM. Thus, probable physiological targets of ATM phosphorylation can be identified. Where the cellular processes that these targets affect are known, this assay can establish a likelihood that the cellular process is regulated, at least in part, by ATM.

Second, the ATM kinase substrate polypeptides can be used to screen for ATM kinase agonists or antagonists. Since the chimeric polypeptides have a structural portion, which may provide for specific binding, they can be readily evaluated for phosphorylation. Thus, screening assays for compounds that agonize or antagonize ATM activity can be performed by measuring the level of phosphorylation of the ATM substrate polypeptide, e.g., either with in vitro cell-free or cellular assay methods. Recombinant expression systems can be used to express ATM and ATM substrate polypeptides for cell-free, in vitro assays. Alternatively, cells that express ATM (either endogenously or recombinantly) are engineered to express the ATM substrate polypeptide, so that any physiological effects of the ATM substrate polypeptide on cellular processes can be evaluated.

Third, the ATM substrate polypeptide can be used as a competitive inhibitor of ATM phosphorylation in cellular assays. In one embodiment, the ATM kinase recognition site sequence of the polypeptide is specifically recognized by ATM, but not by DNA-PK, ATR, or other kinases. In another embodiment, the presence of a kinase recognition sequence in the ATM substrate polypeptide only inhibits phosphorylation of the specific target protein from which the sequence was derived, thus specifically affecting one ATM-regulated process. In still another embodiment, the ATM substrate polypeptide has a substrate sequence that is generally recognized by ATM and another kinase or kinases.

In another embodiment, the invention provides ATM functional assays. A stably expressed, dominant-negative kinase dead ATM mutant of the invention can be used to validate these assays, and further permits evaluation of the cellular processes regulated by ATM. The dominant-negative mutant, a competitive inhibitor ATM substrate polypeptide, or an ATM antagonist (or agonist) compound discovered using the screening assays described herein, can be used in assays for ATM function, including in vitro cell-based assays for cell cycle processes, radiation sensitivity, and chemotherapeutic sensitivity, and animal models of ATM function. These cell-based and animal models have direct correlates with therapeutic methods based on modulation, e.g., inhibition, of ATM activity. Inhibition of ATM activity clearly is important in treating tumors, by rendering the tumors more sensitive to radiation or chemotherapeutic agents. Although the prior art has suggested a role for inhibition of ATM in these processes, the discoveries of the present invention permit a detailed understanding of the mechanism by which ATM affects these processes, which in turn permits a more effective, rational approach to targeting therapy for tumors without inhibiting physiologically beneficial ATM activity. Furthermore, these results have unexpected implications for additional therapeutic modalities, including enhancing anti-restenosis strategies based on inhibition of cellular proliferation. The present invention further provides a strategy for targeting ATM-mediated insulin signal transduction by PHASI in adipocytes, for treating obesity. It should be noted that the therapeutic aspects of the invention can be directly evaluated in the animal model assays described herein, and that the animal models substantiate therapeutic potential of ATM modulation.

Thus, the present invention permits more precise analysis of known and discovered ATM-regulated cellular process. The term "cellular process" is used herein to refer to cellular processes, such as, but by no means limited to, double stranded DNA break repair, telomere synthesis or repair, the aging process, tumor suppression, insulin and insulin-like growth factor (IGF)-I signaling, cell cycle control, cell survival after HTLV infection, and autophosphorylation. The invention has advantageously permitted identification of novel cellular processes that are regulated by ATM-mediated phosphorylation of various targeting proteins, such as DNA repair, aging, neurodegeneration, HTLV infection, and significantly, obesity. Furthermore, the discoveries of the invention permit more precise and complete biochemical analysis of processes, such as tumor suppression in conjunction with ionizing radiation and cell cycling. The term "ATM-regulated process" is used herein to refer to a cellular process that depends upon or is affected by ATM-mediated phosphorylation of a target protein.

Accordingly, more extensive descriptions of the various aspects of the invention are provided in the following sections of the application: ATM kinase (including kinase dead mutants); the ATM kinase substrate recognition consensus sequence (including disclosure of ATM target proteins that have this motif); ATM substrate polypeptides (the fusion polypeptides for testing whether a motif sequence is phosphorylated by ATM and for screening assays); crystal structure of ATM-ATM kinase substrate recognition sequence complexes (for rational drug design); recombinant expression systems (for screening, function assays, and therapeutics); screening assays (for identification of modulators of ATM function); assays for ATM function (using dominant-negative ATM and ATM modulator compounds); and modulation of ATM activity for therapy. The headings (bold), subheadings (bold, italics), and sections of the application are provided to facilitate understanding of the invention, and are not intended to be limiting.

General Definitions

In a specific embodiment, the term "about" or "approximately" means within 20%, preferably within 10%, and more preferably within 5% of a given value or range.

As used herein, the term "isolated" means that the referenced material is free of components found in the natural environment in which the material is normally found. In particular, isolated biological material is free of cellular components. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate unrelated materials, i.e., contaminants. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. A purified tumor cell is preferably substantially free of other normal cells. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The use of italics (e.g., ATM) indicates a nucleic acid molecule (cDNA, mRNA, gene, etc.); normal text (e.g., ATM) indicates the polypeptide or protein.

Molecular Biology Definitions

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, A Practical Guide To Molecular Cloning (1984); F. M. Ausubel et al. (eds.), *Current Protocols in Molecular Biology*, John Wiley & Sons, Inc. (1994).

Therefore, if appearing herein, the following terms shall have the definitions set out below.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or functional assays, as described infra. A host cell has been "transfected" by exogenous or heterologous DNA when such DNA has been introduced inside the cell. A cell has been "transformed" by exogenous or heterologous DNA when the transfected DNA is expressed and effects a function or phenotype on the cell in which it is expressed. The term "expression system" means a host cell transformed by a compatible expression vector and cultured under suitable conditions e.g. for the expression of a protein coded for by foreign DNA carried by the vector and introduced to the host cell.

Proteins and polypeptides can be made in the host cell by expression of recombinant DNA. As used herein, the term "polypeptide" refers to an amino acid-based polymer, which can be encoded by a nucleic acid or prepared synthetically. Polypeptides can be proteins, protein fragments, chimeric proteins, etc. Generally, the term "protein" refers to a polypeptide expressed endogenously in a cell, e.g., the naturally occuring form (or forms) of the amino acid-based polymer. Thus, the physiological substrate of ATM kinase is a "target protein", while a chimeric construct comprising an ATM kinase substrate recognition sequence is a "fusion polypeptide."

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The coding sequences herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'- non-coding regions, and the like. The nucleic acids may also be modified by many means known in the art. Non-limiting examples of such modifications include methylation, "caps", substitution of one or more of the naturally occurring nucleotides with an analog, and internucleotide modifications.

The term "gene", also called a "structural gene" means a DNA sequence that codes for or corresponds to a particular sequence of ribonucleic acids or amino acids which comprise all or part of one or more proteins, and may or may not include regulatory DNA sequences, such as promoter sequences, which determine for example the conditions under which the gene is expressed.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background.

A coding sequence is "under the control" or "operatively associated with" of transcriptional and translational control sequences in a cell when RNA polymerase transcribes the coding sequence into mRNA, which then may be trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell.

The term "transfection" means the introduction of a foreign nucleic acid into a cell. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned", "foreign", or "heterologous" gene or sequence, and may include regulatory or control sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." Recombinant cloning vectors will often include one or more replication systems for cloning or expression, one or more markers for selection in the host, e.g. antibiotic resistance, and one or more expression cassettes.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, an gene is heterologous to the recombinant vector DNA in which it is inserted for cloning or expression, and it is heterologous to a host cell containing such a vector, in which it is expressed, e.g., a CHO cell.

The terms "mutant" and "mutation" mean any detectable change in genetic material, e.g. DNA, or any process, mechanism, or result of such a change. This includes gene mutations, in which the structure (e.g., DNA sequence) of a gene is altered, any gene or DNA arising from any mutation process, and any expression product (e.g., protein) expressed by a modified gene or DNA sequence. The term "variant" may also be used to indicate a modified or altered gene, DNA sequence, enzyme, cell, etc., i,e., any kind of mutant.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., *Cell* 50:667, 1987). Such proteins (and their encoding genes) have sequence homology, as reflected by their sequence similarity, whether in terms of percent similarity or the presence of specific residues or motifs.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or 95% of the nucleotides match over the defined length of the DNA sequences, as determined by sequence comparison algorithms, such as BLAST, FASTA, DNA Strider, etc.

Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

The present invention provides antisense nucleic acids (including ribozymes), which may be used to inhibit expression of ATM kinase, or alternatively an ATM kinase target protein, e.g., to disrupt a cellular process. An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607).

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, e.g., for cloning full length or a fragment of a protein or polypeptide. In a further embodiment, an oligonucleotide of the invention can form a triple helix with a nucleic acid (genomic DNA or mRNA) encoding a protein or polypeptide. Generally, oligonucleotides are prepared synthetically, preferably on a nucleic acid synthesizer. Accordingly, oligonucleotides can be prepared with non-naturally occurring phosphoester analog bonds, such as thioester bonds, etc. Furthermore, the oligonucleotides herein may also be modified with a label capable of providing a detectable signal, either directly or indirectly. Exemplary labels include radioisotopes, fluorescent molecules, biotin, and the like.

Specific non-limiting examples of synthetic oligonucleotides envisioned for this invention include oligonucleotides that contain phosphorothioates, phosphotriesters, methyl phosphonates, short chain alkyl, or cycloalkl intersugar linkages or short chain heteroatomic or heterocyclic intersugar linkages. Most preferred are those with $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. Nos. 5,792,844 and No. 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O-; S-, or N-alkyl; O-, S-, or N-alkenyl; $SOCH_3$; $SO_2CH_3$; $ONO_2$; $NO_2$; $N_3$; NH2; heterocycloalkyl; heterocycloalkaryl; aminoalkylamino; polyalkylamino; substitued silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

ATM Kinase

The methods and compositions of the present invention relate, in particular, to the activity of an ATM kinase. As used herein, the term "ATM kinase" (or "ATM") refers to a polypeptide that phosphorylates target proteins that have an ATM kinase substrate recognition consensus sequence motif, as described herein, or the nucleic acid (cDNA or genomic DNA) encoding such an ATM kinase. Such ATM kinases include human ATM kinase described in U.S. Pat. No. 5,756,288, U.S. Pat. No. 5,728,807, and U.S. Pat. No. 5,777,093, including both wild-type and naturally occurring mutant ATM kinases. Naturally occurring mutant ATM kinases are either truncated or are unstable proteins. The invention further advantageously provides an engineered, non-naturally occurring, kinase-dead ATM, which behaves as a dominant-negative mutant and is preferred for use in ATM function assays as described herein. In a specific embodiment, the dominant-negative kinase-dead mutant has an amino acid sequence assigned accession number 1585222, and is encoded by a cDNA having a nucleotide sequence assigned accession number U33841, in the NCBI database. The term also encompasses non-human ATM kinases, which can be used in the various assays and methods of the invention.

Methods for obtaining an ATM gene are well known in the art, (see, e.g., Sambrook et al., 1989, supra). The DNA may be obtained by standard procedures known in the art from cloned DNA (e.g., a DNA "library"), and preferably is obtained from a cDNA or genomic library prepared from tissues with high level expression of the protein, by chemical synthesis, by cDNA cloning, or by the cloning of genomic DNA, or fragments thereof, purified from the desired cell (see, e.g., Sambrook et al., 1989, supra; Glover, D. M. (ed.), 1985, supra), or as described in the ATM patents cited above. Whatever the source, the gene should be molecularly cloned into a suitable vector for propagation of the gene.

Further selection can be carried out on the basis of the properties of the gene, e.g., if the gene encodes a protein product having the isoelectric, electrophoretic, amino acid composition, partial or complete amino acid sequence, antibody binding activity, ligand binding profile, particularly ATM kinase substrate binding specificity, or enzymatic activity of ATM protein as disclosed herein. Thus, the presence of the gene may be detected by assays based on the physical, chemical, immunological, or functional properties of its expressed product.

The present invention also relates to assay and expression systems that employ cloning vectors containing genes encoding wild-type ATM, or analogs and derivatives of ATM that have the same or homologous functional activity as ATM. Thus, although ATM per se is a well-known protein, its expression and use in assays of the invention, such as the in vitro cell-free screening assay, is contemplated. The production and use of derivatives and analogs related to ATM are within the scope of the present invention. In a specific embodiment, the derivative or analog is functionally active, i.e., capable of exhibiting one or more functional activities associated with a full-length, wild-type ATM of the invention. Chimeric fusion proteins with ATM, such as FLAG, GST, or HIS-tagged ATM, are contemplated, as are fusion proteins that contain functional domains (discussed below).

ATM derivatives can be made by altering encoding nucleic acid sequences by substitutions, additions or deletions that provide for functionally equivalent molecules. Preferably, derivatives are made that have enhanced or increased functional activity relative to native ATM. In another embodiment, exemplified infra, a kinase dead derivative of ATM can be prepared. Preferably, the kinase dead derivative (or mutant) is dominant-negative.

Due to the degeneracy of nucleotide coding sequences, other DNA sequences which encode substantially the same amino acid sequence as an ATM gene may be used in the practice of the present invention. These include but are not limited to allelic genes, sequence variants of ATM, and functional variants of ATM (see, infra).

The genes encoding ATM derivatives of the invention can be produced by various methods known in the art. The sequence can be cleaved at appropriate sites with restriction endonuclease(s), followed by further enzymatic modification if desired, isolated, and ligated in vitro. In the production of the gene encoding a derivative of ATM, care should be taken to ensure that the modified gene remains within the same translational reading frame as the ATM gene, uninterrupted by translational stop signals, in the gene region where the desired activity is encoded.

Additionally, the ATM-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., J. Biol. Chem. 253:6551, 1978; Zoller and Smith, DNA 3:479–488, 1984; Oliphant et al., Gene 44:177, 1986; Hutchinson et al., Proc. Natl. Acad. Sci. U.S.A. 83:710, 1986), use of TAB linkers (Pharmacia), etc. PCR techniques are preferred for site directed mutagenesis (see Higuchi, 1989, "Using PCR to Engineer DNA", in *PCR Technology: Principles and Applications* for DNA Amplification, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids.

Optimization of Dominant-Negative ATM

Mutant forms or fragments of ATM can function as dominant-negative molecules when expressed exogenously (Morgan et al., Mol. Cell Biol., 17:2020, 1997). However, an ATM fragment construct can be quite unstable in its expression in human cells and prove difficult to use in many settings. One advantage of the invention is in providing ATM constructs that inhibit wild-type ATM function in cells for studies in both cell culture and animal models.

In each case, cDNA's after transfection or infection into cells in culture are used to evaluate various aspects of ATM dysfunction, including assays for the $G_2/M$ checkpoint, S-phase checkpoint and radiosensitivity (both MTT and clonogenic survival), as described more fully infra.

Full-length kinase-dead mutant. A full-length mutant ATR expressed exogenously appears to have dominant-negative activity (Cliby et al., EMBO J, 17:159, 1998). A kinase-dead full length ATM mutant which can be stably expressed has been generated (Example 1, infra; NCBI protein database accession no. 1585222 for the amino acid sequence and accession no. U33841 for the cDNA sequence). In one embodiment, such a full-length dominant-negative ATM is prepared by mutating an amino acid corresponding to residue Asp-2870 of ATM, e.g., to Ala, or mutating an amino acid residue corresponding to Asn-2875, e.g., to Lys, or preferably both. Both stable transfectants and transient transfectants of various cell lines can be made and tested for loss of ATM function by the variety of assays described herein.

ATM fragments. The full-length ATM cDNA is over 9kb in length and is thus quite difficult to manipulate. This large size also places significant restrictions on vectors that can be used to introduce the cDNA, with particular limitations on viral vectors. Thus, one further advantage of the invention is the discovery of a more reliable and facile way to genetically manipulate ATM function in tumor cells. In particular, some ATM functions have been inhibited with a small fragment containing the leucine zipper region of ATM. Recombinant ATM chimeric fragment expression can be tested with a variety of available antibodies directed against ATM protein and/or with antibodies directed against an epitope tag, such as FLAG or GST, which can be placed on either the 5' or 3' end of the expressed sequence.

ATM fragments which may be tested include: (i) a smaller version of FB2F, the leucine zipper region of ATM; (ii) the amino-terminal half of the protein from translation start site through the middle of the protein; (iii) the entire protein with just the kinase domain deleted; (iv) the carboxyl-terminal half of the protein. These fragments are tested for the ability to both complement and inhibit ATM function. If a fragment complements (and appears to have kinase activity), then a kinase-dead version of the fragment, which theoretically could act as a dominant-negative peptide and is more easily manipulated and expressed than full length ATM cDNA's, whether wild-type or mutant, is prepared.

ATM Kinase Substrate Recognition Consensus Sequence Motif(s)

An important breakthrough of the present invention is identification of ATM kinase substrate recognition sequences, and a consensus sequence motif for these sequences. Through use of reiterative sequence changes in fusion polypeptides used in in vitro kinase assays, a substrate motif has been defined for the ATM kinase. The basic motif recognized by ATM is:

$B_1$—X—$B_2$—S—Q—X—X  (SEQ ID NO:1)

where $B_1$ is a hydrophobic amino acid, $B_2$ is a hydrophobic amino acid or aspartate, X is any amino acid, Q is glutamine, and S is serine (the amino acid which is phosphorylated by ATM). A number of different sequences fitting this motif have been tested and two sequences appear to provide the optimal target sequence. These two sequences are:

P—P—D—S—Q—E—X  (SEQ ID NO:2)

and

L—P—[L or A]—S—Q—[D or P]—X  (SEQ ID NOS:3–6)

where P is proline, D is aspartic acid, E is glutamic acid, L is leucine, A is alanine, and X is again any amino acid.

By analyzing proteins for the presence of a sequence corresponding to the consensus sequence motif using sequence comparison algorithm, such as those mentioned below, it is possible to identify proteins which are physiologic targets of the ATM kinase, termed herein "ATM target proteins". A sequence corresponds to the motif when it has the defining amino acid residues in the appropriate positions relative to each other. One known ATM target protein is p53. Once such physiological targets are identified, the cellular processes involved in phosphorylation (or inhibition of phosphorylation) by the ATM kinase can be characterized. Identification of such processes permits one to screen for and optimize small molecule inhibitors or inducers of ATM kinase activity to agonize or antagonize a particular cellular process. Clarification of these sequences also distinguishes ATM substrate specificity from other related kinases, such as ATR and DNA-PK. These clarifications aid in the development of modulators with enhanced specificity for the ATM kinase. Summaries of the putative motifs for each of these three kinases as defined by the in vitro kinase assays of the invention are shown in Table 4 in Example 3.

In a specific embodiment, a reiterative approach is used to identify consensus putative target motifs for ATM and related kinases. Beginning with the amino terminal p53 target sequence containing serine 15, which we have identified as an ATM target (Example 2), a plasmid fusing this peptide sequence in-frame with a GST sequence can be generated and then expressed in bacteria. The GST-fusion polypeptide is purified and then used as a target in the in vitro kinase assay using ATM, and optimally ATM-kinase dead, ATR, and/or DNA-$PK_{cs}$ as the kinase. Selected mutations can be made in the p53 (or other) target sequence to determine which mutations were capable of altering (either decreasing or increasing) the ability of the kinase to phosphorylate the serine residue of interest.

Insights gained from this mutagenesis approach allow further definition of the putative target sequence for the ATM (and other) kinases. Searching sequence databases permits identification of proteins containing serine residues in sequences which are potential physiological targets of ATM. These sequences can be generated in the GST-plasmid (Example 1) and another GST-fusion polypeptide was thus available for testing (as demonstrated in Example 3). The results from testing such known sequences permit further refinement of the target consensus motif, which may then be used in a reiterative manner to identify other potential physiologic target proteins of the ATM kinase.

As shown in Example 3, using the in vitro kinase assay and various peptide substrates to elucidate phosphorylation site motifs, we have been able to screen protein databases for putative kinase targets for ATM. Candidate peptide sequences from these proteins were tested for their ability to be phosphorylated by ATM in the in vitro kinase assay. This accomplishes two goals: 1) further refinement of the ATM kinase substrate motif and, 2) identification of potential physiologic targets of the ATM kinase, which can be tested for physiologic relevance in intact cells. The list of proteins and sites below represents the proteins, and sites within those proteins, which represent valid in vitro targets for the ATM kinase. It should also be noted that this approach not only identifies protein targets, but it simultaneously provides the invaluable information about which site in the protein is phosphorylated. Such information leads to rapid insights into the physiological significance of phosphorylation events.

A set of proteins which contain sequences and are potential ATM target proteins identified using this approach are listed below (Table 1). Subsequently, more quantitative experiments (Example 3) established that some ATM substrate peptides are not highly phosphorylated. In a preferred aspect of the invention, proteins that contain putative substrate sequences that demonstrate at least about 20% of the level of phosphorylation as the p53 peptide with S15 are considered good candidates for regulation or activation by ATM. However, phosphorylation of a putative substrate peptide indicates a high probability, but not a certainty, that the protein is a target of ATM phosphorylation in vivo. Thus, preferably, putative ATM phosphorylation site peptides show at least about 20% of the phosphorylation of the p53 site containing S15.

TABLE 1

Proteins Containing Sequences Phosphorylated by ATM

| ATM Targets | Activity | Phosphorylation Site Sequence | SEQ ID NO: |
| --- | --- | --- | --- |
| 53 (in vivo) | Tumor suppression | SVEPPLSQETFSDL | 7 |
| NBS/p95 | DNA Nijmegen Breakage syndrome | TPGPSLSQGVSVDE | 10 |
| MRE11 (SQ1) | Double strand DNA break repair | QQLFYISQPGSSVV | 11 |
| PHAS1 | Insulin signaling (obesity) | EPPMEASQSHLRNS | 9 |
| CHK1 (SQ1) | Cell cycle check point | NVKYSSSQPEPRTG | 16 |
| WERNER (SQ1) | Aging | EKAYSSSQPVISAQ | 21 |
| CHK1 (SQ2) | Cell cycle check point | VQGISFSQPTCPDH | 17 |
| PTS1 | Tumor suppression | WETPDLSQAEIEQK | 37 |
| CUT1 | Spindle check point | GASPVLSQGVDPRS | 36 |

TABLE 1-continued

Proteins Containing Sequences Phosphorylated by ATM

| ATM Targets | Activity | Phosphorylation Site Sequence | SEQ ID NO: |
|---|---|---|---|
| ATM440 | Autophosphorylation | PLLMILSQLLPQQR | 24 |
| BRCA1 (SQ2) | Breast cancer | DCSGLSSQSDILTT | 33 |
| RAD17 (SQ1) | DNA damage responses | TWSLPLSQDSASEL | 18 |
| RAD17 (SQ2) | DNA damage responses | ASELPASQPQPFSA | 19 |

As discussed below, several of these proteins are of great physiologic interest in and of themselves and even greater interest is generated by the fact that they may be physiologic targets of ATM.

Identification of protein sequences which do not appear to be targets of the ATM kinase has almost as much potential physiologic significance as identifying the proteins which are targets. For example, ATM plays a role in phosphorylating serine 15, but not serine 37, of p53 after DNA damage, but both are thought to be important modifications of the protein after DNA damage. This approach allows us to conclude that serine 37 is not a target of ATM, but is a reasonable target for DNA-PK$_{cs}$. Similarly, we are able to conclude that the DNA repair enzyme, ligase IV, which contains a putative substrate sequence for any member of this family of kinases, is phosphorylated by DNA-PK$_{cs}$, but not by ATM. Examples of proteins which have sequences which could serve as potential targets, but do not seem to be targets in our assays, are also listed below (Table 2).

TABLE 2

Examples of proteins whose sequences were not phosphorylated in vitro by ATM

| Protein | Peptide Sequence (putative phosphorylation site) | SEQ ID NO. |
|---|---|---|
| TP1 | SPLAPVSQQGWRSI | 45 |
| CABL | YPGIDLSQVYELLE | 23 |
| ATM (S2761) | YKVVPLSQRSGVLE | 25 |
| ATR | TVEPIISQLVTVLL | 22 |
| PI-3K | DLLMYLSQLVQALK | 26 |
| GEF | RLRPLLSQLGGNSV | 27 |
| DNA POL-δ | LPCLEISQSVTGFG | 30 |
| E4F | APEPPVSQELPCSR | 31 |
| BRCA2 | KVSPYLSQFQQDKQ | 29 |
| β-ADAPTIN | CRAPEVSQHVYQAY | 28 |
| MRE11 (SQ2) | FSVLRFSQKFVDRV | 12 |
| MRE11 (SQ3) | RARALRSQSEESAS | 13 |
| MRE11 (SQ4) | SASRGGSQRGRAFK | 14 |

BRCA2, another familial breast cancer gene product, appears to be phosphorylated by ATR, but not by ATM. The peptide sequence in BRCA2 recognized by ATR is: KVSPYLSQFQQDKQ (SEQ ID NO:29). Another example of distinctions which can be drawn with this approach is that the related kinase, DNA-PK, can phosphorylate both serine 15 and 37 in p53 while ATM phosphorylates only serine 15.

Based on these data, and the kinase target motif sequences shown in Table 3, we were able to evaluate kinase specificity for substrate sequences.

TABLE 3

Kinase Target Motif Sequences

| KINASE | N − 5 | N − 4 | N − 3 | N − 2 | N − 1 | N* | N + 1 | N + 2 | N + 3 | N + 4 |
|---|---|---|---|---|---|---|---|---|---|---|
| ATM | X | X | P/M/I/G/F/Y | X | D/I/A/S/L (B except D) | S | Q | X | X | X |
| "BEST | — | — | P | P | D | S | Q | E | X | — |
| TARGET" | — | — | L | P | L/A | S | Q | D/P | X | — |
| DNA-PK | V/L | X | P | X | L/P | S/T | Q | E/A | X | F/D |
| ATR | X | X | L/P | X | L/A/V | S/T | Q | X | X | X |

B = hydrophobic
N* = site of phosphorylation

ATM, a serine kinase, depends on hydrophobic residues immediately amino terminal to SQ at N−3 and N−1; it is unaffected by substitutions which are carboxyl terminal to N+1 or amino terminal to N−3.

DNA-PK, a serine-threonine kinase similar to ATM, but exhibits some activity on threonine and depends on V at N−5 and E/A and F/D at N+2 and N+4 respectively.

ATR, a serine-threonine kinase which is similar to ATM, exhibits some activity on threonine and is insensitive to changing N−1 in the p53 amino terminal sequence to valine (this change abrogates ATM activity).

Of interest for the present invention is identification of polypeptide sequences that contain a putative ATM kinase substrate recognition sequence but cannot be phosphorylated. Such sequences can bind to the active site of ATM and competitively inhibit ATM phosphorylation of target proteins. Accordingly, such a sequence is termed herein a "competitive ATM kinase substrate recognition sequence". In a specific embodiment, such sequences lack an amino acid residue that is phosphorylated by ATM kinase, e.g., serine or, to a lesser extent, threonine.

ATM Target Proteins

Using the consensus motif, various proteins were identified by computer analysis as containing putative ATM kinase substrate recognition sites. A simple algorithm written to search the human protein database was used to identify sequences corresponding to a preliminary motif based on sequences from p53 and PHASI. These sites were introduced into chimeric constructs (described infra) and tested for phosphorylation by ATM. Based on this analysis, a number of ATM target proteins in addition to p53 have been identified.

Furthermore, allelic variants, degenerate coding sequences, truncated derivative ATM target proteins containing the ATM substrate recognition site, and ATM target protein derivatives with conserved amino acid substitutions (function conservative variants), and the nucleic acids encoding such variants and derivatives, can also be prepared. The function (where known) of these proteins, and the role of ATM in regulating the activity of these target proteins is discussed below:

p53 is the most commonly mutated gene in human cancer. It plays a critical role in helping cells respond to cytotoxic stresses, such as ionizing irradiation, DNA base damage, hypoxia, etc. Serine 15, but not serine 37, is phosphorylated by ATM. This protein is important for both tumor development and tumor responses to therapy.

NBS is the protein produced by the gene mutated in the "Nijmegen Breakage Syndrome". Children with this genetic disorder are similar to those with Ataxia-telangiectasia (AT), except that they exhibit microcephaly and do not exhibit ataxia. NBS protein has recently been shown to be part of a protein complex that forms at sites of double strand DNA breaks and appears to be critical for normal responses and repair following DNA breakage. It is likely that ATM and NBS function in the same pathway in helping cells respond to ionizing radiation. This observation provides the first biochemical link between the two.

MRE11 is a part of the DNA double strand break repair complex (along with NBS), establishing a further link between ATM and DNA damage responses. Identification of the sites which are phosphorylated in both NBS and MRE 11 focuses attention on these sites as having particular physiologic relevance, and facilitates understanding their roles (by providing potential sites within these proteins to mutate in functional assays) and mechanisms of action in DNA damage response pathways.

PHASI is a member of the PHAS family that appears to be primarily expressed in adipocytes. PHAS proteins regulate protein translation in response to a number of stimuli, including insulin stimulation. The site in PHASI identified as a putative ATM target is not present in the other related PHAS proteins, suggesting that ATM activity is solely directed to PHASI in adipocytes. This observation may help explain the extremely thin nature of AT patients and potentially provides a novel mechanism for obesity treatment as it relates to fat production.

CHK1 is a cell cycle checkpoint protein involved in controlling cell cycle progression following DNA damage. Proteins with this function probably play important roles in both cancer development and determining cellular responses following exposure to DNA damaging agents, such as irradiation and chemotherapy. We have identified two putative ATM target sites within CHK1; this will facilitate understanding the specific roles (by providing potential sites within CHK1 to mutate in functional assays) and mechanisms of action of CHK1.

Werner's protein is a recently identified gene product which is mutated in Werner's Syndrome, a dramatic syndrome of premature aging. The protein appears to be a DNA helicase and identification of this protein as an ATM target facilitates understanding of both diseases and the functions of both of these proteins.

PTS 1 is our designation ("putative tumor suppressor") for a gene located on chromosome 3 on the 'p' arm at 3p21.3, which has not yet been named (GenBank accession number 3834393). The chromosomal location of the gene is a very common site of chromosomal loss in a variety of carcinomas. In a search for the important tumor suppressor gene on chromosome 3p21.3 in small cell lung cancer, this gene was identified and the complete DNA sequence of this gene was recently submitted to the sequence databases. Using the "reiterative" approach detailed herein, this peptide sequence proved to be an excellent in vitro target of the ATM protein kinase. Subsequent data with a fragment of this protein of about 100 amino acids confirm this observation. The discovery that this protein, which may be the long sought after '3p' tumor suppressor, is a target of ATM kinase provides insights that could greatly facilitate understanding the role and mechanism of action of the protein, which may be important.

CUT1 is a protein which appears to be involved in the formation of mitotic spindles and thus plays a critical role in cell cycle progression. Little is known about its mechanism of action, but identification of the ATM phosphorylation site provides for investigating mechanistic questions. Since mitotic checkpoints have potential relevance as targets for cancer treatments, this may turn out to have therapeutic relevance as well as importance for general cell biology.

ATM is a phosphoprotein, and our data suggest that it can be autophosphorylated. Examining the sequence of ATM uncovered a number of potential sites, and one peptide sequence has been identified as autophosphorylated at amino acid residue 440 by ATM. This discovery provides novel insights into regulation of ATM function and may be used to inhibit ATM function in selected pathways, such as specifically in radiation-induced responses, without altering other aspects of ATM function. This has particular relevance in the optimal development of a inhibitor of ATM to be used for radiosensitization clinically.

BRCA 1 is a gene which has been identified as an important familial breast cancer susceptibility gene. The protein product of BRCA1 has been implicated in DNA damage response pathways, but there is still a poor level of understanding of BRCA1 function. Identification of this protein as an ATM target provides insights into breast cancer development and treatment and into general aspects of radiation biology ranging from tumor development to tumor response to therapy.

hARD17 is the human homolog of a gene product which is a critical cell cycle checkpoint protein in yeast. Its relevance to human disease is not known, but identification of this protein as a target of ATM provides important insights into the understanding of radiation responses and has implications for tumor responses to therapy. This observation has the potential to lead to the identification of other targets for enhancing the radiosensitivity of human tumors.

ATM Substrate Polypeptides

The present invention further provides chimeric proteins that contain putative ATM kinase substrate recognition sequences (termed herein "ATM substrate polypeptides"), including nucleic acids encoding such ATM substrate polypeptides, and vectors for expression of such ATM substrate polypeptides for in vitro (e.g., cell free), ex vivo (e.g., cell line-based), or in vivo assays. Because the present invention provides the sequence recognized by ATM for phosphorylation, in a preferred embodiment, fusion polypeptides comprising a putative or known ATM kinase recognition sequence from a protein can be prepared and tested for binding to or phosphorylation by ATM, e.g., in a cell-free in vitro assay as exemplified in Example 1. Alternatively, ATM kinase target proteins discussed in greater detail in the section above can also be used in various assays for ATM kinase enzymatic (i e., phosphorylation) activity.

ATM substrate polypeptides can be obtained using the molecular biological techniques described in connection with ATM, supra.

As used herein, the term "fusion polypeptide" refers to a chimeric construct comprising a structural portion and an ATM kinase substrate recognition sequence portion. The term "structural portion" refers to a part of the fusion polypeptide that provides a generalized function, such as specific binding, reporter enzymatic activity, or that literally supplies sufficient secondary, tertiary, and/or quaternary structure so that ATM kinase can bind to and phosphorylate the substrate recognition sequence portion. Examples of structural portions include, but are not limited to, FLAG, GST, and HIS-tag. FLAG and GST are readily recognized by antibodies, and permit immunoseparation, e.g., immunoprecipitation or detection by immunoassay (similar epitope tags can be included in recombinant ATM, as described above, or recombinant ATM target proteins). A HIS-tag permits chromatographic separation on a nickel (Ni)-chelation column. Examples of structural portions with reporter activity include β-galactosidase, chloramphenicol transferase, horseradish peroxidase, alkaline phosphatase, luciferase, and green fluorescent protein. Other possible structural portions include antibody Fc portions, targeting molecules such as hormones or transferrin, or any other polypeptide that has a desired sequence. Preferably the structural portion does not itself contain a sequence that is phosphorylated by ATM kinase, i.e., it lacks an ATM kinase substrate recognition sequence. This ensures that only the putative substrate recognition sequence portion of the fusion polypeptide will be phosphorylated (if at all).

The term "ATM kinase substrate recognition sequence" refers to a sequence that has (termed a known recognition sequence) or appears to have (termed a putative recognition sequence) an ATM kinase substrate recognition sequence, i.e., it has a sequence corresponding to the ATM kinase substrate recognition consensus sequence motif. As exemplified infra, any putative ATM kinase substrate recognition sequence portion can be joined with the structural portion and tested for recognition and phosphorylation by ATM. Using chimeric constructs of the invention, a number of ATM kinase substrate recognition sequences have been identified; other sequences containing serine have been eliminated as not phosphorylated by ATM. In a specific embodiment, the sequence phosphorylated by ATM is selected from the following group:

SVEPPLSQETFSDL (SEQ ID NO:7); TPGPSLSQGVS-VDE (SEQ ID NO: 10);
QQLFYISQPGSSVV (SEQ ID NO:11); EPP-MEASQSHLRNS (SEQ ID NO:9);
NVKYSSSQPEPRTG (SEQ ID NO:16); EKAY-SSSQPVISAQ (SEQ ID NO:21);
VQGISFSQPTCPDH (SEQ ID NO:17); WETP-DLSQAEIEQ (SEQ ID NO:37);
GASPVLSQGVDPR (SEQ ID NO:36); PLLMILSQLL-PQQR (SEQ ID NO:24);
DCSGLSSQSDILTT (SEQ ID NO:33); TWSLPLSQD-SASEL (SEQ ID NO:18); and
ASELPASQPQPFSA (SEQ ID NO:19).

In a further embodiment, a substrate recognition sequence in the fusion polypeptide can bind ATM without being phosphorylated, e.g., a competitive ATM kinase substrate recognition sequence. Such competitive sequences can be identified using the binding and phosphorylation assays of the invention.

To assay for phosphorylation activity, ATM kinase is contacted with a fusion polypeptide and phosphorylation of the fusion polypeptide is detected. This approach has, for example, permitted refinement of the consensus sequence motif by establishing whether a putative recognition sequence is phosphorylated by ATM kinase.

Binding activity of a fusion polypeptide with ATM can be tested, e.g., by a competitive assay, immunoassay, or other standard method in the art. The physiological relevance of phosphorylation of the fusion polypeptide can be confirmed by testing with the target protein from which the recognition sequence was obtained; further analysis can involve evaluating the effects on cellular processes, as described in greater detail infra.

Furthermore, the substrate recognition sequence of a target protein can be systematically mutated in a fusion polypeptide to further explore the sequence specificity of ATM kinase, as exemplified infra.

The fusion polypeptides can also be used to identify an optimal target sequence for ATM, either through mutagenesis or by testing sequences from putative target proteins. An optimized ATM kinase substrate recognition sequence may be distinguished from other kinase recognition sequences, as exemplified, infra.

A fusion polypeptide comprising an ATM kinase substrate recognition sequence fused to a non-target, or structural, amino acid sequence can be produced by any means. In one embodiment, such a fusion polypeptide is produced by recombinant expression of a nucleic acid encoding the protein (comprising an ATM kinase substrate recognition-coding sequence joined in-frame to a structural coding sequence). The nucleic acid can be made by ligating the appropriate nucleic acid sequences encoding the desired amino acid sequences to each other by methods known in the art, which are described herein, in the proper reading frame, and expressing the chimeric product by methods commonly known in the art. Chimeric genes comprising putative ATM kinase substrate recognition sequence portions fused to any heterologous protein-encoding sequences may be constructed. Alternatively, it is possible to prepare such a fusion polypeptide by synthetic or semi-synthetic methods, including solid phase peptide synthesis or peptide condensation synthesis, or a combination thereof.

Crystal Structure of ATM Kinase

Knowledge of the ATM kinase substrate recognition sequence can provide a theoretical basis for predicting the structure of potential modulations, such as agonists or antagonists, of the protein. Identification and screening of modulators is further facilitated by determining structural features of the recognition sequence, e.g., using X-ray crystallography, neutron diffraction, nuclear magnetic resonance spectrometry, and other techniques for structure determination. These techniques provide for the rational design or identification of agonists and antagonists of ATM kinase.

In particular, when designing or optimizing small molecule inhibitors, it is extremely helpful to have a crystal structure of the target molecule. This is a particular challenge with ATM because of its enormous size (approximately 370kd peptide). Crystallization may be performed either with the full length protein or with an expressed fragment containing the kinase domain. At this time, it appears that the "Rad3" fragment in the C-terminal half of the protein is expressed at reasonable levels in mammalian cells. Full-length ATM has been successfully expressed in baculovirus. Thus, either full-length ATM or Rad3 ATM can be used for crystallization studies. Initial characterizations of either ATM or "Rad3" proteins includes limited proteolysis and domain analysis. This may aid in identifying an optimal peptide to use for crystallization.

In a preferred embodiment, a composition comprising ATM and an ATM substrate polypeptide (containing an ATM kinase substrate recognition site) are provided for co-crystallization (or other structure-function studies). The polypeptide can be a peptide having the recognition sequence, an ATM substrate polypeptide, or a fragment of an ATM target protein containing the recognition sequence. In specific embodiments, one of the sequences disclosed herein is employed. In another embodiment, co-crystallization is performed in a manganese-free solution to prevent phosphorylation and discharge of the substrate polypeptide.

Recombinant Expression Systems

The present invention contemplates various cloning and expression vectors for expression of the proteins and polypeptides described herein, including without limitation ATM kinase, ATM kinase-dead mutants and other ATM derivatives, target proteins, mutated target proteins, ATM substrate polypeptides, and the like. Such expression vectors can be used to transform cells in vivo or in vitro for ATM kinase activity assays, or the investigates the role of ATM or cellular processes. Furthermore, recombinant expression systems can be used to produce ATM and target proteins or substrate polypeptides for extracellular activity and binding assays. The molecular biological techniques described above can be used to prepare expression systems of the invention.

A wide variety of host/expression vector combinations (i.e., expression systems) may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMa1-C2, pET, pGEX (Smith et al., Gene 67:31–40, 1988), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. An example of a mammalian cell expression system of the invention includes, but is by no means limited to, 293T cells, as exemplified infra. In addition, various tumor cells lines can be used in expression systems of the invention.

Expression of the protein or polypeptide may be controlled by any promoter/enhancer element known in the art, but these regulatory elements must be functional in the host selected for expression. Promoters which may be used to control gene expression include, but are not limited to, cytomegalovirus (CMV) promoter, the SV40 early promoter region (Benoist and Chambon, 1981, Nature 290:304–310), the promoter contained in the 3' long terminal repeat of Rous sarcoma virus (Yamamoto, et al., Cell 22:787–797, 1980), the herpes thymidine kinase promoter (Wagner et al., Proc. Natl. Acad. Sci. U.S.A. 78:1441–1445, 1981), the regulatory sequences of the metallothionein gene (Brinster et al., Nature 296:39–42, 1982); prokaryotic expression vectors such as the β-lactamase promoter (Villa-Komaroff, et al., Proc. Natl. Acad. Sci. U.S.A. 75:3727–3731, 1978), or the tac promoter (DeBoer, et al., Proc. Natl. Acad. Sci. U.S.A. 80:21–25, 1983); see also "Useful proteins from recombinant bacteria" in Scientific American, 242:74–94, 1980; promoter elements from yeast or other fungi such as the Gal 4 promoter, the ADC (alcohol dehydrogenase) promoter, PGK (phosphoglycerol kinase) promoter, alkaline phosphatase promoter.

Expression Vectors

Preferred vectors, particularly for cellular assays in vitro and animal models or therapeutics in vivo or ex vivo, are viral vectors, such as lentiviruses, retroviruses, herpes viruses, adenoviruses, adeno-associated viruses, vaccinia viruses, baculoviruses, and other recombinant viruses with desirable cellular tropism. Thus, a gene encoding a functional or mutant protein or polypeptide can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 7:980–990, 1992). Preferably, the viral vectors are replication defective, that is, they are unable to replicate autonomously in the target cell. Preferably, the replication defective virus is a minimal virus, i.e., it retains only the sequences of its genome which are necessary for encapsidating the genome to produce viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 2:320–330, 1991; International Patent Publication No. WO 94/21807, published Sept. 29, 1994; International Patent Publication No. WO 92/05263, published Apr. 2, 1994); an attenuated adenovirus vector, such as the vector described by Stratford-Perricaudet et al. (J. Clin. Invest. 90:626–630, 1992; see also La Salle et al., Science 259:988–990, 1993); and a defective adeno-associated virus vector (Samulski et al., J. Virol. 61:3096–3101, 1987; Samulski et al., J. Virol. 63:3822–3828, 1989; Lebkowski et al., Mol. Cell. Biol. 8:3988–3996, 1988).

Various companies produce viral vectors commercially, including but by no means limited to Avigen, Inc. (Alameda, CA; AAV vectors), Cell Genesys (Foster City, CA;

retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, Nature Medicine, 1995). In that regard, it is advantageous to employ a viral vector that is engineered to express a minimal number of antigens.

Adenovirus vectors. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g., Manhattan or A26/61 strain (ATCC VR-800), for example). Various replication defective adenovirus and minimum adenovirus vectors have been described (WO94/26914, WO95/02697, WO94/28938, WO94/28152, WO94/12649, WO95/02697 WO96/22378). The replication defective recombinant adenoviruses according to the invention can be prepared by any technique known to the person skilled in the art (Levrero et al., Gene 101:195 1991; EP 185 573; Graham, EMBO J. 3:2917, 1984; Graham et al., J. Gen. Virol. 36:59 1977). Recombinant adenoviruses are recovered and purified using standard molecular biological techniques, which are well known to one of ordinary skill in the art.

Adeno-associated viruses. The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques.

Retrovirus vectors. In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, EP178220; Bernstein et al. Genet. Eng. 7 (1985) 235; McCormick, BioTechnology 3 (1985) 689; International Patent Publication No. WO 95/07358, published Mar. 16, 1995, by Dougherty et al.; and Kuo et aL., 1993, Blood 82:845. The retroviruses are integrating viruses which infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Suitable packaging cell lines have been described in the prior art, in particular the cell line PA317 (U.S. Pat. No. 4,861,719); the PsiCRIP cell line (WO 90/02806) and the GP+envAm-12 cell line (WO 89/07150). In addition, the recombinant retroviral vectors can contain modifications within the LTRs for suppressing transcriptional activity as well as extensive encapsidation sequences which may include a part of the gag gene (Bender et al., J. Virol. 61:1639, 1987). Recombinant retroviral vectors are purified by standard techniques known to those having ordinary skill in the art.

Retrovirus vectors can also be introduced by recombinant DNA viruses, which permits one cycle of retroviral replication and amplifies tranfection efficiency (see WO 95/22617, WO 95/26411, WO 96/39036, WO 97/19182).

Lentivirus vectors. In another embodiment, lentiviral vectors are can be used as agents for the direct delivery and sustained expression of a transgene in several tissue types, including brain, retina, muscle, liver and blood. The vectors can efficiently transduce dividing and nondividing cells in these tissues, and maintain long-term expression of the gene of interest. For a review, see, Naldini, Curr. Opin. Biotechnol., 9:457–63, 1998; see also Zufferey, et al., J. Virol., 72:9873–80, 1998). Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virusparticles at titers greater than 106 IU/ml for at least 3 to 4 days (Kafri, et al., J. Virol., 73: 576–584, 1999). The vector produced by the inducible cell line can be concentrated as needed for efficiently transducing nondividing cells in vitro and in vivo.

Non-viral vectors. In another embodiment, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner, et. al., Proc. Natl. Acad. Sci. U.S.A. 84:7413–7417, 1987; Felgner and Ringold, Science 337:387–388, 1989; see Mackey, et al., Proc. Natl. Acad. Sci. U.S.A. 85:8027–8031, 1988; Ulmer et al., Science 259:1745–1748, 1993). Useful lipid compounds and compositions for transfer of nucleic acids are described in International Patent Publications WO95/18863 and WO96/17823, and in U.S. Pat. No. 5,459,127. Lipids may be chemically coupled to other molecules for the purpose of targeting (see Mackey, et. al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector in vivo as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., J. Biol. Chem. 267:963–967, 1992; Wu and Wu, J. Biol. Chem. 263:14621–14624, 1988; Hartmut et al., Canadian Patent Application No. 2,012,311, filed March 15, 1990; Williams et al., Proc. Natl. Acad. Sci. USA 88:2726–2730, 1991). Receptor-mediated DNA delivery approaches can also be used (Curiel et al., Hum. Gene Ther. 3:147–154, 1992; Wu and Wu, J. Biol. Chem. 262:4429–4432, 1987). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., C.P. Acad. Sci., 321:893, 1998; WO 99101157; WO 99/01158; WO 99/01175).

Screening Assays

Based on the present invention, a program to screen compounds or libraries of compounds for their ability to modulate phosphorylation by ATM kinase can be implemented. Modulation of ATM activity includes increasing (agonizing) or inhibiting (antagonizing) ATM binding to ATM substrate polypeptides or ATM target proteins, or ATM-mediated phosphorylation of substrate polypeptides or target proteins. Using either full-length ATM or fragments containing the kinase domain, compounds which modulate ATM kinase activity can be screened. After initial identification and preliminary characterizations, such candidate modulator compounds may be evaluated in cell-based and animal model assays in order to determine their ability to function as modulators of ATM function (described in the following section).

Any screening technique known in the art can be used to screen for ATM agonists or antagonists. For example, various binding assays for ATM binding to polypeptides that comprise an ATM kinase substrate recognition sequence or a competitive kinase substrate recognition sequence can be employed.

In general, screening for a compound that modulates ATM-mediated phosphorylation involves detecting whether there is a change in the level of ATM-mediated phosphorylation of an ATM substrate polypeptide or a novel ATM target protein in the presence of a candidate compound, e.g., using the cell-free in vitro assay described above and in Example 1. An increase in the level of phosphorylation indicates that the compound agonizes ATM-mediated phosphorylation, and a decrease in the level of phosphorylation indicates that the compound antagonizes ATM-mediated phosphorylation. Preferably, the compound selectively modulates ATM-mediated phosphorylation, i.e., without affecting other kinases, such as ATR or DNA-PK.

In a further embodiment, the screen can provide for detecting inhibition of a cellular process mediated by ATM phosphorylation of a target protein, wherein inhibition of the activity is indicative of inhibition of ATM as described in Example 4. For example, the cellular process may be loss of S-phase checkpoint, a defect in the $G_2/M$ checkpoint, an increase in radiosensitivity, or increase in sensitivity to chemotherapeutic agents. Preferably, particularly for primary screening, the cellular process involves an novel ATM target protein.

In still another embodiment, the screen provides for detecting a compound that induces an ATM-regulated process in a cell, comprising contacting the cell with a candidate compound, and detecting whether the ATM-mediated process is induced in the cell. Preferably, the cell is defective for expression of ATM, or is modified to express a dominant-negative ATM mutant.

In another embodiment, various reporter gene assays can be used to evaluate changes in gene expression as a result of modulation of ATM activity by a test compound. Preferably, the reporter gene expression is tied to ATM-mediated phosphorylation. This can be accomplished by introducing an ATM kinase substrate recognition sequence into a signal transduction protein upstream of the reporter gene, or by inserting a reporter gene into a gene whose expression is induced (or suppressed) in an ATM-regulated fashion. In a preferred embodiment, reporter gene expression is controlled by an ATM target protein, especially a novel target protein as described herein. Reporter genes include green fluorescent protein (GFP), luciferase, β-galactosidase (β-gal or lac-Z), chloramphenicol transferase (CAT), horseradish peroxidase, and alkaline phosphatase. In addition, expression levels of almost any protein can be detected using a specific antibody.

As used herein, the term "compound" refers to any molecule or complex of more than one molecule that affects ATM function. The present invention contemplates screens for synthetic small molecule agents, chemical compounds, chemical complexes, and salts thereof as well as screens for natural products, such as plant extracts or materials obtained from fermentation broths. Other molecules that can be identified using the screens of the invention include proteins and peptide fragments, peptides, nucleic acids and oligonucleotides (particularly triple-helix-forming oligonucleotides), carbohydrates, phospholipids and other lipid derivatives, steroids and steroid derivatives, prostaglandins and related arachadonic acid derivatives, etc.

One approach to identifying such a compound uses recombinant bacteriophage to produce large libraries. Using the "phage method" (Scott and Smith, Science 249:386–390, 1990; Cwirla, et al., Proc. Natl. Acad. Sci., 87:6378–6382, 1990; Devlin et al., Science, 49:404–406, 1990), very large libraries can be constructed ($10^6$–$10^8$ chemical entities). A second approach uses primarily chemical methods, of which the Geysen method (Geysen et al., Molecular Immunology 23:709–715, 1986; Geysen et aL J. Immunologic Method 102:259–274, 1987; and the method of Fodor et al. (Science 251:767–773, 1991) are examples. Furka et al. (14th International Congress of Biochemistry, Volume #5, Abstract FR:013, 1988; Furka, Int. J. Peptide Protein Res. 37:487–493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists. In another aspect, synthetic solid phase combinatorial libraries (Needels et al., Proc. Natl. Acad. Sci. USA 90:10700–4, 1993; Ohlmeyer et al., Proc. Natl. Acad. Sci. USA 90:10922–10926, 1993; Lam et al., International Patent Publication No. WO 92/00252; Kocis et al., International Patent Publication No. WO 9428028) and the like can be used to screen for ATM ligands according to the present invention.

Assays for Modulation of ATM Function

Screening for ATM function and modulation of ATM function involves cell-based or animal model-based assays. Such assays can be used as secondary screens for the activity of candidate compounds selected in a primary screen, e.g., the cell-free kinase assay described above and in Example 1. Furthermore, the assays for candidate ATM inhibitor compounds (antagonists) can be validated with a positive control—the dominant-negative ATM mutant. Certain assays of the invention provide improvements over conventional assays, and the present invention contemplates such improved cell-based assays or ATM function as falling within its scope. Moreover, either an ATM inhibitor discovered herein, or a dominant-negative mutant, can be used to establish ATM-regulated pathways in cells. These models are also useful to evaluate the effects of ATM inhibition on the function of other treatments, such as radiation and chemotherapy.

Cell-Based Assays

S-phase checkpoint. Loss of the S-phase checkpoint is one of the pathognomonic features of cells lacking ATM function. This is a more difficult checkpoint to assess than the $G_1/S$ checkpoint and, in the past, required a relatively cumbersome assay of incorporation of $^3$H-thymidine at very early time points after irradiation. The present invention optimizes aspects of this assay to enhance its reliability and ease of use. Furthermore, a sensitive and reliable non-radioactive, flow cytometric assay using incorporation of the thymidine analog, BrdUrd, at early time points after irradiation can be implemented.

$G_2/M$ Checkpoint. The defect in the $G_2/M$ checkpoint in AT cells is an unusual one. Only cells which are in $G_2$ at the time of irradiation fail to arrest in $G_2$ and enter mitosis (normal cells will not enter mitosis) in this setting. AT cells which are in S-phase at the time of irradiation will arrest when they get into $G_2$. In a typical cell cycle analysis using flow cytometry, the increase in the number of $G_2$ cells after irradiation is actually a result of irradiated S-phase cells accumulating in $G_2$, and it takes at least a few hours to begin to see this effect. In order to assess the defect in the $G_2/M$ checkpoint in AT cells, it has been necessary to actually do mitotic spreads on cells at early time points after irradiation and count the number of mitotic cells at various times after irradiation (Morgan et al., Mol. Cell. Biol., 17:2020, 1997). In such a scenario, after 30 minutes, there will be a decrease in the number of mitotic figures if cells arrest in $G_2$ (normal cells) and there will be little to no decrease in mitotic figures at these time points after irradiation in cells defective in the $G_2/M$ checkpoint (e.g., AT cells).

A more rapid, objective quantitative assay for this $G_2/M$ checkpoint as another assessment of ATM function in cells is provided. Two-color flow cytometry using a combination of PI may be used to assess DNA content and a mitotic specific antibody conjugated to FITC. For example, an antibody to phosphorylated Histone 113 (which is phosphorylated only in mitosis) and antibodies specific for phosphorylated MPM2 (which is also phosphorylated only in mitosis) can be used to assess mitotic state of cells. The ability to distinguish the $G_2$ cells (4N content DNA, H-P negative) and M cells (4N content DNA, H3-P positive) allows accurate quantization of the number of $G_2$ and M cells and easy assessment of the ability of $G_2$ cells to arrest prior to M at these early time points. This assay can serve as a facile way to test inhibitors for their ability to inhibit ATM function.

Radiosensitivity. Another classic feature of loss of ATM function is enhanced radiosensitivity. The standard for assessing radiosensitivity has typically been clonogenic survival assays. However, this is a long and somewhat cumbersome assay. The present invention provides for utilization of MTT assays for a rapid assessment of increased radiosensitivity caused by ATM dysfunction. An optimized MTT assay may be used to quickly screen compounds for their ability to increase cellular radiosensitivity and promising compounds can be checked with standard clonogenic survival assays.

Sensitivity to agents other than ionizing radiation. AT cells have also been reported to exhibit increased sensitivity to radiomimetic drugs, like bleomycin. Though the concomitant use of a systemic drug along with an ATM inhibitor would be difficult because of increased toxicity to normal tissues, such a drug conjugated to a molecule which targets the drug to the tumor could potentially be used successfully in combination with ATM inhibition. For example, conjugating a drug to an antibody directed against a ganglioside, such as GD2, would target that drug to neuroblastoma cells. Concurrent use of an ATM inhibitor may significantly enhance the sensitivity of the tumor cell to the tumor-directed drug. Similarly, an antibody against Her2-neu could be used in such a combination to more effectively treat a subset of breast cancers. This is similar to the use of brachytherapy (see below), but uses a drug conjugated to the antibody or other targeting molecule rather than a radioisotope. This concept is further developed below.

Candidate compounds can be tested for enhanced sensitivity in AT cells. One example of compounds for testing are the calicheamicins, which have been reported to be more toxic in AT cells (Sullivan and Lyne, Mut. Res., 245:171, 1990) and have been successfully conjugated to an antibody in the treatment of neuroblastoma cells (Lode et al., Cancer Res., 58:2925, 1998). Other compounds can be similarly tested and candidate compounds can be tested in the model animal systems as well.

Transfectants. A variety of tumor cell lines can be transfected both stably and transiently and tested in the various ATM functional assays. These cell lines include: H1299; MEF's, which may be extended to use a variety of MEF's with selected genetic abnormalities; MCF-7 breast carcinoma cells; SY5Y neuroblastoma cells; and RKO colerectal carcinoma cells.

As a precursor for potential introduction of ATM dominant-negative cDNA's into tumors in vivo, any of the above ATM fragments that exhibit dominant-negative activity can be introduced into a variety of tumor cells, e.g., with adenoviral vectors, AAV, retroviral vectors, or lentiviral vectors. Inhibition of ATM activity is assessed as described above. Such vectors can also be used to administer the ATM-inhibiting gene to tumors in vivo and assess in vivo radiosensitization (see below).

ATM Function in Animal Models

Dominant-negative ATM cDNAs and ATM antagonists or agonists can be used to initiate investigations in vivo relating to optimal use of candidates selected as a result of the screen for ATM kinase modulators, particularly inhibitors, or to evaluate ATM-mediated cellular processes. Animal models of the therapeutic modulation of ATM can also be prepared to evaluate ATM function.

Xenograft models. Xenografts of cell lines, particularly tumor cell lines, stably or transiently expressing a dominant-negative ATM cDNA construct are generated. (Testing for loss of ATM-function is done in an in vitro cell assay, as described above.) Using mouse xenograft model systems, increased sensitivity of tumors expressing ATM-inhibitory activities is used to compare radiosensitivity of these tumors to tumors generated from parental (unmodified) cell lines. Toxicity to normal tissues is examined. The results of exposure to selected chemotherapeutic agents, particularly agents to which AT cells should exhibit increased sensitivity (see above), is evaluated. Excellent mouse xenograft tumor models have been developed (Zamboni et al., J. Natl. Cancer Inst., 90:505, 1998) for testing tumor cell sensitivity, and such model systems can be employed for these studies.

"Brachytherapy" models. Brachytherapy is discussed in detail in the therapeutic section below.

Any number of different in vivo tumor model systems may be used to test brachytherapeutic approaches. One preferred model system uses neuroblastoma cell lines. Antibodies directed against the GD2 ganglioside are available and have been used both in vivo and in vitro to direct toxins or radioisotopes to tumor cells. Thus, paired neuroblastoma cells with and without ATM dominant-negative vectors may be generated, and their sensitivity to GD2-radioconjugates in the xenograft model system evaluated. Many other model systems and tumor types can be similarly tested.

Animal model systems also allow characterization of directed delivery of other cytotoxic agents in conjunction with ATM inhibition. In this case, ATM inhibition is effected in combination with a non-radioactive compound (which may be a highly desirable option for clinicians), for example, to explore conjugation of enedienes, like calicheamicin or neocarzionstatin (NCS), to GD2 antibodies for testing in the neuroblastoma models. AT cells exhibit increased sensitivity to NCS and calicheamicin, and modified calicheamicins have been designed with specific toxicity to tumor cells (Nicolaou et al., Science, 256:1172–1178, 1992). In addition, calicheamicin $\theta^1$ has been successfully conjugated to GD2 antibodies and used to treat neuroblastoma in a mouse model system (Lode et al., Cancer Res., 58:2925–2928, 1998). Thus, such calicheamicin-conjugated anti-CD2 can be used in the xenograft models discussed above in conjunction with ATM inhibition by using the paired neuroblastoma models (with and without ATM dominant-negative expression). Other antibodies and model tumor systems can also be used, but the basic design and questions will basically be the same. These experiments will facilitate use of a small molecule ATM inhibitor in conjunction with tumor-targeted cytotoxins.

Modulation of ATM Activity for Therapy

The present invention provides for modulating the activity of ATM kinase, either by inhibiting or increasing the level of ATM-mediated phosphorylation, as indicated for treatment of a particular disease state. For example, for enhancing cellular radiosensitivity, inhibition of ATM is desirable. Other pathological cellular processes, such as premature aging, may be blocked or reduced by increasing ATM mediated phosphorylation. Thus, a particular advantage of the present invention lies in the ability to modulate ATM-regulated processes by modulating ATM-mediated phosphorylation of target proteins. Moreover, the specificity of phosphorylation vis a vis other kinases, which has been described above and in the Examples, infra, permits specifically targeting cellular processes, but leaving other processes unaffected.

ATM activity can be inhibited by various means, including by delivery of a dominant-negative ATM derivative (e.g., a kinase-dead mutant) to cells, by antisense nucleic acids (including ribozymes and triple-helix-forming oligonucleotides; these are described in detail supra), and by expression of anti-ATM intracellular antibodies, e.g., single chain Fv antibodies (see generally Chen, Mol. Med. Today 3:160–167, 1997; Spitz et al., Anticancer Res. 16:3415–3422, 1996; Indolfi et al., Nat. Med. 2:634–635, 1996; Kijima et al., Pharmacol. Ther. 68:247–267, 1995). In an alternative, small molecules discovered by methods of the present invention and peptides identified herein can be used to inhibit ATM activity.

ATM activity can be enhanced by increasing the level of expression of ATM in a cell, in vitro or in vivo. In a specific embodiment, the level of ATM activity is increased by transferring an expression vector for ATM to the cell. In another embodiment, small molecules discovered by methods of the present invention can be used to induce ATM activity.

Any of the vectors and delivery methods disclosed above can be used for modulation of ATM activity, e.g., in a therapeutic setting. As disclosed infra, the therapeutic methods of the invention are optimally achieved by targeting the therapy to the affected cells. Means for targeting delivery of various treatments, such as radiation or chemotherapy, are described below. However, in another embodiment, an ATM inhibitor or an ATM stimulator can be targeted to cells, e.g., using the vectors described above in combination with well-known targeting techniques, for expression of ATM modulators.

Furthermore, any of the therapies described herein can be tested and developed in animal models. Thus, the therapeutic aspects of the invention also provide assays for ATM function.

Cancer

ATM is a particularly attractive target for inhibition in a clinical setting because the increased radiosensitivity of cells lacking ATM function includes the low doses of radiation (1–2 Gy) typically used clinically for tumor therapy. In addition, multiple doses or low-dose rate (brachytherapy) might be expected to enhance the effects of sensitization associated with ATM inhibition.

Radiosensitize tumors to external beam irradiation. Systemic application of this technology to all forms of cancer could be problematic because of increased toxicity to normal tissues resulting from ATM inhibition. However, the radiosensitivity of both AT patients and AT-knockout mice appears to be largely confined to the GI tract, so the increased radiosensitization of normal tissues may not present a problem if the GI tract (mouth to rectum) is not in the radiation field. Thus, primary usage for tumors like brain tumors (glioblastoma multiforme in particular) and peripheral tumors such as bone tumors is envisioned. Moreover, with well-focused beams, one could inhibit ATM in other tumors, like breast and lung carcinomas. ATM inhibition can also enhance sensitivity of metastatic lesions, e.g., such as bony metastases in prostate cancer.

Brachytherapy by local delivery of radioconjugates and chemotherapeutics.

Directing the cytotoxic exposure directly to the tumor itself is a commonly used approach to deliver a cytotoxic drug while minimizing the cytotoxic exposure of normal tissues. However, one of the factors which limits the effectiveness of such an approach is incomplete induction of tumor cell death because of limited dose delivery. Thus, it would be highly desirable to concurrently use an ATM inhibitor to enhance the sensitivity of the tumor cells to the particular cytotoxic agent. Concurrent use of ATM inhibitor with the tumor-targeted delivery of a radioisotope in an animal model is particularly indicated. Tumor specific delivery is commonly achieved by conjugating a cytotoxic agent to an antibody that preferentially targets the tumor.

Cytotoxic agents include toxins (such as ricin) and radioisotopes. An ATM inhibitor is desirable for targeted radiotherapy because radiation is long-term and low dose, and ATM inhibition would be expected to effectively sensitize cells to this dose delivery mode. The targeting may be done with natural targeting (i.e., with radioactive iodine in the treatment of thyroid carcinoma), physical targeting (ie., administration of a radioisotope to a particular body cavity), a tumor-specific antibody (e.g., anti-CD2 in neuroblastoma or anti-Her2-neu in certain breast carcinomas), or other targeting protein (e.g., ferritin in hepatocellular carcinoma).

Using the same concepts discussed above for radioisotopes, local delivery of certain chemotherapeutic agents could be used in combination with ATM inhibition. For example, AT cells exhibit enhanced sensitivity to enedienes such as calicheamicin, presumably because these drugs induce DNA strand breaks. Thus, conjugation of calicheamicin to an antibody directed against GD2 (Lode et al., Cancer Res., 58:2925, 1998) could be used in combination with an ATM inhibitor to treat neuroblastoma.

This approach could similarly be used for any other tumor for which a specific antibody exists (e.g., anti-Her2neu in breast cancer).

Cardiovascular Disease

A major problem facing cardiologists following the use of balloon angioplasty to open up blocked coronary arteries is re-stenosis of those arteries over the ensuing several months. One approach to inhibit such restenosis currently under investigation involves administration of radioisotopes via catheter to the coronary artery after angioplasty to try to inhibit endothelial cell proliferation. This appears to work well in porcine models. Concomitant administration of an ATM inhibitor with the radioisotope would enhance the anti-proliferative effects.

Another approach is to use anti-proliferative drugs capable of blocking endothelial cell proliferation. For example, a drug like calicheamicin, which induces DNA strand breaks, would be effective, particularly in combination with an ATM inhibitor to enhance the effectiveness of the drugs. This chemotherapeutic approach reduces dependence on radiation oncologists and physicists.

Revascularization

Furthermore, the "T" in AT stands for "telangiectasias", which is proliferation of small blood vessels. Interestingly, in AT patients, these tend to occur on sun-exposed areas, like facial skin and sclerae. Clinically, AT patients appear to have a propensity to neoangiogenesis in mucosal areas exposed to toxic insults. For example, GI mucositis can lead to bleeding varicies months after the chemotherapy-induced mucositis, and hemorrhagic cystitis appears months after treatment of AT patients with Cytoxan. In both cases, this appears to represent a "hyperproliferation" of blood vessels in response to mucosal injury and reflects the same pathophysiology which results in telangiectasias in sun-exposed areas in AT patients. Thus, it is envisioned that not only will an ATM inhibitor used concomitantly with a radioisotope or cytotoxic drug in a coronary artery after angioplasty inhibit restenosis more effectively, it might also result in helpful neoangiogenesis, e.g., restoration of blood vessels after treatment of an occlusion.

Obesity

It has been demonstrated that the ATM kinase phosphorylates a protein called PHASI. The site in PHASI which gets phosphorylated has been identified as serine 94. Interestingly, PHASI is involved in translational regulation and is a critical part of signaling from the insulin receptor. Highly phosphorylated PHASI is expressed at very high levels in adipocytes, and is expressed at low levels or is nearly absent in other cell types. There are two closely related family members, PHASII and III, which are expressed in many cell types. Moreover, though these three proteins are highly homologous, the serine 94 (target site for ATM) is present only in PHAS I. This ATM phosphorylation of PHAS proteins in response to insulin may only occur in adipocytes.

It has been clinically reported that there is a mild form of insulin resistance in AT patients, especially those on steroids, which is poorly understood mechanistically. The clinical observation has also been made that AT patients are extraordinarily thin and have virtually no subcutaneous fat. The present discovery, that ATM phosphorylates PHASI, suggests that lack of ATM function in AT patients prevents insulin signaling to adequately stimulate growth of adipocytes. Therefore, inhibition of ATM may prevent insulin signaling in adipocytes and may thus be used to treat obesity. Other ATM target proteins specific for adipocytes could be reasonable targets to inhibit in reducing obesity or fat generation, and the present invention permits identification of such targets. Targeting ATM inhibition to adipocytes may prevent adipocyte growth without resulting in systemic exposure.

Retroviral Infections, Including HIV

ATM is a target in the development of treatments for retroviral infections, particularly human T cell leukemia virus (HTLV) infections. HTLV-I is linked to the generation of a certain form of T-Cell leukemia, and HTLV-III, also known as human immunodeficiency virus (HIV), is the causative agent of acquired immune deficiency syndrome (AIDS). An ATM inhibitor may be used to block retroviral infection by leading to the death of cells into which an HTLV virus attempts to integrate.

DNA-PK is necessary for the repair of double-stranded DNA breaks. It has recently been reported that attempted retroviral integration in cells that lack DNA-PK results in apoptosis (Daniel et al., Science, 284:644–647, 1999). Cell death is due to unrepaired double-stranded DNA breaks that arise during retroviral integration. Retroviral integration is thus lethal to double-strand break repair deficient cells.

DNA-PK shares structural and functional properties with ATM, including the presence of a protein kinase domain in the carboxyl terminal region of the protein. In addition, both enzymes appear to be involved in the repair of DNA double strand breaks. ATM deficient cells do not tolerate the integration of exogenous DNA and are sensitive to agents that cause DNA double strand breaks. Based on the present discovery, retroviral integration is expected to be lethal to ATM-deficient cells.

An inhibitor of ATM kinase, discovered by the screening procedure proposed in this application, may be used as a reagent for the treatment of retroviral infections, particularly HTLV-I or HTLI-III (HIV) infections. HTLV-I and HTLI-III both integrate into the genome of lymphocytes. Treatment of lymphocytes with an ATM inhibitor is expected to lead to death of the lymphocytes upon attempted retroviral integration. The death of lymphocytes into which retroviruses attempt to integrate thus has clinical utility for the treatment of either HTLV-I or HTLV-III (HIV) infection, particularly during or after current combination therapy (with reverse transcriptase and protease inhibitors). ATM inhibition under these circumstances can "mop up" any residual, infectious virus to delay or prevent recurrence of high viral titers and onset of AIDS.

One advantage of the use of an ATM inhibitor for the treatment of HTLV infections is that the host cell, rather than the virus, is targeted for treatment. Targeting the host cells circumvents neutralization of many therapies resulting from the ability of the HIV virus to rapidly mutate, leading to resistance to treatments that target the virus. HTLV viruses must integrate into a host cell for successful infection, and consequently would not be able to survive a drug that leads to the death of any cell into which the virus attempts to integrate.

An ATM kinase inhibitor may work in concert with current treatment regimes that target the HIV virus and is expected to reduce or prevent the ability of the virus to infect new lymphocytres. ATM inhibitors thus are clinically useful adjunct approaches to the treatment of retroviral infections such as AIDS or HTLV-I induced leukemias.

EXAMPLES

The present invention will be further understood by reference to the following examples, which are provided as exemplary of the invention and not by way of limitation.

Example 1
An In Vitro Assay for ATM Kinase Function

ATM Constructs. The full-length cDNA encoding $NH_2$-terminal, FLAG-tagged wild-type ATM (Ziv et al., Oncogene, 15:159–167, 1997) was excised from pFB-YZ3 and subcloned into the XhoI site of pcDNA3 (Invitrogen) generating pcDNA-FLAG-ATMwt. To generate catalytically inactive ATM, a cDNA fragment encoding the PI3 kinase-related domain of ATM (Morgan et al., Mol. Cell. Biol., 17:2020–2029, 1997) was mutated by overlap PCR substituting Asp 2870 with Ala and Asn 2875 with Lys. A cDNA fragment encoding the kinase domain was excised from wild type ATM and replaced with a Bpu 1101 I-XhoI fragment containing the mutations described above generating pcDNA-FLAG-ATMkd.

Transfection and Kinase Activity Assays. 293T cells were transiently transfected with 10 μg of either pcDNA-FLAG-ATMwt, pcDNA-FLAG-ATMkd, pBJF-FRPwt or pBJF-FRPkd (Cliby et al., EMBO J., 17:159, 1998) using calcium phosphate and harvested two days later. Cells were lysed through sonication in TGN buffer [50 mM Tris (pH 7.5), 50 mM glycerophosphate, 150 mM NaCl, 10% glycerol, 1% Tween 20, 1 mM NaF, 1 mM $NaVO_4$, 1 mM PMSF, 2 μg/mg Pepstatin A, 5 μg/ml leupeptin, 10 μg/ml Aprotinin and 1 mM DTT] as described (Brunn et al., Science, 277:99–101, 1997). After centrifugation at 13,000 xg, 2 mg of extract were incubated with mouse IgG and protein A/G sepharose beads (Calbiochem). FLAG-tagged proteins were then immunoprecipitated with anti-FLAG M2 monoclonal antibody (Eastman Kodak Company) and protein A/G sepharose beads. Immunoprecipitates were washed twice with TGN buffer, once with 100 mM Tris (pH 7.5) plus 0.5 M LiCl, and twice with kinase buffer [10 mM Hepes (pH 7.5), 50 mM glycerophosphate, 50 mM NaCl, 10 mM $MgCl_2$, 10 mM $MnCl_2$, 5 μM ATP, and 1 mM DTT]. Kinase reactions were initiated by resuspending washed beads in 30 μl of kinase buffer containing 10 μCi [γ-$^{32}$P]ATP and 1 μg GSTp53$_{1-101}$ and incubated for 30 minutes at 30° C. Proteins were electrophoretically separated by SDS-polyacrylamide gel electrophoresis, transferred to nitrocellulose, and analyzed on a PhosphorImager. FLAG-tagged proteins and GSTp53$_{1-101}$ were subjected to immunoblotting with either anti-FLAG M2 antibody or monoclonal antibodies directed towards the NH2-terminus of p53 (Ab-2 and Ab-6, Calbiochem) as described (Siliciano et al., Genes Dev., 11:3471, 1997).

Example 2
Activation of ATM Kinase by Ionizing Radiation

The p53 tumor suppressor protein is activated and phosphorylated on Ser$^{15}$ in response to various DNA damaging agents. The gene product mutated in Ataxia telangiectasia, ATM, acts upstream of p53 in a signal transduction pathway initiated by ionizing irradiation. The present Example demonstrates that immunoprecipitated ATM had intrinsic protein kinase activity and phosphorylated p53 on Ser$^{15}$ in a $Mn^{+2}$-dependent manner. Ionizing radiation, but not ultraviolet radiation, rapidly enhanced this p53-directed kinase activity of endogenous ATM. These observations, along with the fact that phosphorylation of p53 on Ser$^{15}$ in response to ionizing radiation is reduced in AT cells, suggest that ATM is a protein kinase that phosphorylates p53 in vivo. Furthermore, the system used to evaluate phosphorylation of p53 is generally applicable in screening assays of other ATM kinase target proteins, and could be used for screening for compounds that modulate ATM-mediated phosphorylation. These data are published (Canman et al., Science 281:1677–1679, 1998).

Materials and Methods

Phosphorylation of Ser$^{15}$ of p53 by ATM and ATR/FRP1 in vitro. 293T/17 cells were transfected with expression vectors encoding FLAG-tagged wild type (wt) or catalytically inactive (kd) ATM or ATR/FRP 1. After 48 hours, ATM or ATR was immunoprecipitated and used in the in vitro kinase assay with [γ$^{32}$P]ATP and either wt, S6A, S9A, or S15A GSTp53$_{1-101}$ as substrates. Proteins from each reaction were separated by SDS polyacrylamide gel electrophoresis (7% gel), transferred to nitrocellulose, and analyzed either on a PhosphorImager or by immunoblotting. Amounts of FLAG-tagged ATM or ATR in each kinase reaction were measured by immunoblotting with anti-FLAG M2 (top panel) and amount of [γ$^{32}$P]phosphate incorporated into ATM or ATR during the reaction (lower panel). Levels of phosphorylation in the in vitro kinase assay with wt GSTp53$_{1-101}$ or various mutant GSTp53$_{1-101}$ proteins (S6A, S9A, or S15A) as substrates were determined by immunoblotting for p53. An upper immunoreactive band represents phosphorylated GSTp53 fusion protein. The same exposures were used for ATM, ATR/FRP1 and corresponding substrate proteins.

Fusion Proteins. GSTp53$_{1-101}$ fusion protein was made by amplifying cDNA encoding the first 101 amino acids of human p53 by PCR and subcloning the fragment into the EcoRI and BamHI sites of pGEX-2T (Pharmacia). Serines 6, 9, or 15 were substituted with alanine using the QuikChange Site-Directed Mutagenesis kit according to manufactures suggestions (Stratagene). GSTp53$_{1-101}$ wild type and mutant proteins were individually expressed in bacteria and purified on glutathione-conjugated agarose beads.

Posttranslational modification of p53 on Ser$^{15}$ in response to ionizing radiation. Monoclonal antibodies against a chemically synthesized p53 phosphoserine-15 peptide (amino acids 9–22) were used to immunoblot synthetic peptides (1×, 50 μg) consisting of the first 24 amino acids of p53 with (1–24$^{S15-P}$) or without (1–24) phosphoserine 15. Normal WT (2184) or AT (1526) lymphoblasts were untreated or treated with 5 Gy IR (IR) or 20 mM ALLN for 90 min. p53 was immunoprecipitated, subjected to SDS-PAGE (7.5% gel), transferred to nitrocellulose, and immunoblotted with the monoclonal antibody to phosphoserine 15 p53 (upper panel). Blots were then stripped and immunoblotted with antibodies to p53 (lower panel).

Normal (2184) and AT (1526) EBV immortalized human lymphoblasts were irradiated with a $^{137}$Cs source or treated with 20 mm ALLN (Sigma) for 90 min. Cells were then harvested, lysed, and p53 was immunoprecipitated as described (Siliciano et al., Genes Dev., 11:3471, 1997). Immunoprecipitates were resolved by non-reducing SDS-PAGE, transferred to nitrocellulose and immunoblotted with monoclonal antibody to phosphoserine 15. Blots were stripped and reprobed with p53-specific monoclonal antibodies (Ab-2 and Ab-6).

Assay for activation of endogenous A TM kinase by ionizing radiation in vivo. 2184 or 536 individual normal lymphoblasts or 1526 AT lymphoblasts (AT) were either untreated or treated with 5 Gy IR and harvested 20 or 60 min later. ATM was immunoprecipitated and assayed with wild type GSTp53$_{1-101}$ protein as a substrate. Amounts of ATM present in each reaction were determined by immunoblotting with anti-ATM (Ab-3) and the amount of radiolabel incorporated into ATM during the kinase reaction was visualized with a PhosphorImager. Amounts of [γ$^{32}$P]phosphate incorporated into GSTp53$_{1-101}$ during each reaction was visualized with a PhosphorImager (upper panel). Serine 15 phosphorylation of GSTp53$_{1-101}$ was determined by immunoblotting with anti-phosphoserine 15 p53. 2184 and 536 lymphoblasts were treated with IR or 10 J/m$^2$ V. Endogenous ATM was immunoprecipitated and used in an in vitro kinase assay with GSTp53$_{1-101}$ as substrate. The amount of $^{32}$P-labeled GSTp53$_{1-101}$ was quantitated with a PhosphorImager and normalized to that obtained with immunoprecipitates from unirradiated cells.

Cells were either irradiated or treated with ultraviolet irradiation as described (Canmann et al., Cancer Res., 54:5054, 1994). Endogenous ATM was immunoprecipitated from 3 mg of lysate with ATM-specific rabbit polyclonal antibody (Ab-3, Calbiochem) and subjected to the in vitro kinase assay. The beads and reaction mixtures were separated, resolved by SDS-PAGE and transferred onto Immobilon-P (Millipore) for ATM or nitrocellulose for GSTp53$_{1-101}$. Radiolabeled proteins were visualized and quantitated on a PhosphorImager using ImageQuant software (Molecular Dynamics). Membranes were then immunoblotted with antibodies to ATM (Ab-3) or phosphoserine 15.

Results

We tested whether ATM might also phosphorylate p53 on Ser$^{15}$ and whether the activity of ATM towards p53 as a substrate is regulated by ionizing irradiation. Furthermore, most naturally occurring ATM mutant proteins are unstable (Watters et al., Oncogene, 14:191, 1997). Because a catalytically-inactive ATM mutant is a critical control for in vitro kinase assays, we constructed such a mutant that can be stably expressed. The putative kinase domain of ATM resides in the COOH-terminus of the protein. In related proteins, three critical amino acids within this domain are necessary for phosphotransferase activity (Savitsky et al., Science, 268:1749, 1995; Hunter, Cell, 83:1, 1995). Thus, a recombinant, FLAG-tagged, wild-type ATM was used as a source of ATM protein and a FLAG-tagged, mutant ATM expression construct was generated in which two of the three critical amino acid residues required for catalysis were mutated (D2870A and N2875K). Wild-type and mutant recombinant ATM proteins were individually expressed in 293T cells and in vitro kinase activity was assessed. Equivalent amounts of wild type (wt) and mutant (kd) ATM recombinant proteins were immunoprecipitated and incubated with [γ-$^{32}$p] ATP and recombinant glutathione S-transferase-conjugated p53 protein containing the first 101 amino acids of p53 (GSTp53$_{1-101}$). Although the proteins could be detected with an anti-FLAG or anti-p53 antibody, only the wild type enzyme phosphorylated GSTp53$_{1-101}$. ATM did not phosphorylate GST alone.

Endogenous p53 becomes phosphorylated on Ser$^{15}$ and one other serine residue within the first 24 amino acids of the protein in response to IR (Siliciano et al., Genes Dev., 11:3471, 1997). We tested whether mutation of each of the four serine residues (S6, S9, S15, S20) within the first 24 amino acids of p53 altered the ability of ATM to phosphorylate the NH$_2$-terminus of p53. Recombinant ATM was immunoprecipitated and used to phosphorylate wt or mutant GSTp53$_{1-101}$. Wild-type recombinant ATM phosphorylated wt p53, S6A and S9A mutant p53 but not S15A mutant p53 protein. Similar results were obtained with synthetic peptides comprising the first 24 amino acids of p53 (data as above). Therefore, ATM or a closely associated kinase phosphorylates GSTp53$_{1-101}$ exclusively on Ser$_{15}$ in vitro. Wild-type ATM kinase also showed autophosphorylation in this assay. Because mutation of Asp2870 and Asn2875 within the kinase domain of ATM abolished both phosphorylation of p53 and autophosphorylation of ATM, the kinase activity observed in these assays appears to be intrinsic to the ATM protein. The DNA-PK also phosphorylates Ser$^{15}$ (Lees-Miller et al., Mol. Cell. Biol., 12:5041, 1992), but unlike DNA-PK, ATM was dependent upon the presence of Mn$^{+2}$ and did not require the addition of exogenous DNA for activity (as above).

ATR/FRP-1, another PI-3- kinase related family member, may share functional overlap with ATM in cell cycle checkpoint function (Keegan et al., Genes Dev., 10:2423, 1996; Cliby et al., EMBO J., 17:159, 1998). Conditional expression of catalytically-inactive ATR/FRP-1 abrogates G$_2$-M cell cycle arrest in response to IR. Furthermore, overexpression of wild-type ATR/FRP-1 complements the defective IR-inducible S-phase checkpoint in AT cells. Although ATM is required for rapid phosphorylation of Ser$^{15}$ in response to IR in vivo, ATM appears not to be required when cells are exposed to other genotoxic agents, such as UV irradiation. Thus, other cellular kinases must also phosphorylate p53 on Ser$^{15}$ in vivo. FLAG-tagged recombinant wt ATR/FRP-1 also showed autophosphorylation in vitro that was dependent upon the integrity of the catalytic domain. Like ATM, ATR/FRP-1 phosphorylated p53 on Ser$^{15}$ in a Mn$^{+2}$-dependent manner, though ATR/FRP-1 had at least 20-fold less activity than ATM towards GSTp53$_{1-101}$ when assayed under identical experimental conditions. Thus, p53 appears to be a better substrate for ATM as compared to ATR/FRP-1.

To test whether endogenous p53 required ATM for phosphorylation on Ser$^{15}$ in cells treated with IR in vivo, a monoclonal antibody specific for p53 phosphorylated at Ser$^{15}$ was generated. The p53 protein was immunoprecipitated from normal and AT lymphoblasts either exposed to 5 Gy IR or treated with the proteosome inhibitor, acetyl-Leu- Leu-norleucinal (ALLN), which causes stabilization of p53 protein. Immunoblot analysis with this antibody demonstrated that p53 became phosphorylated only in normal lymphoblasts exposed to IR. Phosphoserine 15 was undetectable in normal cells treated with ALLN, although they accumulated equivalent amounts of total p53 protein to those in irradiated cells. Phosphoserine 15 p53 was also undetectable in the 1526 AT line. Thus, examination of radiation responses in ATM-mutant cells further supports this link between ATM and irradiation-induced phosphorylation of p53.

Activation of endogenous ATM was examined in two different normal lymphoblast cell lines exposed to 0 or 5 Gy IR. ATM immunoprecipitates were used to phosphorylate $GSTp53_{1-101}$ in vitro. Within 20 min after exposure to IR, ATM protein kinase activity toward $GSTp53_{1-101}$ was increased approximately 2-fold. This appeared to be an increase in the specific activity of ATM because the amount of ATM protein did not change in response to IR. Kinase activity towards p53 substrate was minimal in immunoprecipitates from an AT lymphoblast line. The IR-induced activity associated with ATM was directed to $Ser^{15}$ because the immunoprecipitated endogenous ATM from irradiated cells increased phosphorylation of $Ser^{15}$ in in vitro kinase assays. Therefore, ATM kinase appears to be activated in response to IR and phosphorylates p53 on $Ser^{15}$.

Cells derived from AT patients are not hypersensitive to UV irradiation (Lavin and Shiloh, supra, 1997; McKinnon, Hum. Genet., 75:197, 1987). Furthermore, such cells respond normally to UV with increased synthesis of p53, phosphorylation of p53 on $Ser^{15}$, and activation of the stress-activated SAP kinase (JNK) pathway (Canman, et al., Cancer Res., 54:5054, 1994; Kahanna and Lavin, Oncogene, 8:3307, 1993; Siliciano et al., supra, 1997; Shaftman et al., Cancer Res., 55:3242, 1995). The kinase activity of ATM was not increased in cells exposed to UV irradiation. Slight activation of ATM kinase was detected at more than 60 min after exposure, which may be due to signals generated by DNA strand breaks associated with DNA repair (Nelson et al., Mol. Cell. Biol., 14:1815, 1994). These results confirm that ATM plays little role in the cellular UV response and suggests that another kinase other than ATM phosphorylates p53 on $Ser^{15}$ in response to UV irradiation.

Previous genetic and biochemical evidence implicated the ATM gene product in regulating the phosphorylation and induction of p53 in cells exposed to ionizing radiation (Kastan et al., Cell, 71:587, 1992; Siliciano et al., supra, 1997; Xu et al., Genes Dev., 10:2401, 1996; Barlow et al., Nature Genetics, 17:453, 1997). Our results indicate that ATM is a protein kinase whose activity is increased by ionizing irradiation and whose in vivo target may be $Ser^{15}$ of p53. This conclusion is consistent with the finding that ATM and p53 proteins directly interact with each other (Watters et al., Oncogene, 14:1911, 1997). The functional ramifications of radiation-induced $Ser^{15}$ phosphorylation remains to be clearly elucidated. However, phosphorylation of p53 on $Ser^{15}$ reduces binding of the mdm2 oncogene product to p53 in vitro (Shieh et al., Cell, 91:325, 1997) and binding of mdm2 to p53 promotes rapid degradation of p53 by targeting it for proteolytic degradation, thereby potentially controlling p53 protein levels (Haupt et al., Nature, 387:296, 1997; Kubbutat et al., ibid, p. 299). Because many of the clinical manifestations exhibited by AT patients can not be attributed to abnormal regulation of p53 alone, other important targets of the ATM kinase are identified herein.

Example 3

Examination of ATM Kinase Family Substrate Specificities

From the ATM kinase substrate site identified for p53, homologous candidate sites in other proteins were identified and tested, first using the GST-peptide approach, and then with the full length or nearly full length target. This approach identified a number of ATM target proteins.

Based on the fact that p95/nibrin is mutated in an A-T like syndrome, the Nijmegen breakage syndrome, this Example also reports its evaluation as a valid in vitro target. Ionizing irradiation of cells causes ATM-dependent phosphorylation of serine 343 of p95 protein, identical to the in vitro target site for ATM. These observations confirm that ATM participates in signaling to a protein in sensing or modulating repair of DNA damage.

Materials and Methods

Antibodies. The anti-Flag M2 and anti-c-Myc monoclonal antibodies were obtained from Sigma Co. and Roche, respectively. The p95 rabbit polyclonal antibody was described previously (Carney et al., Cell, 93:477–86, 1998). The a-p95-phosphoserine 343 polyclonal antibody was generated by immunizing mice with a KLH-conjugated phosphopeptide (TPGPSL($PO_3$)SQGVSVDE) (SEQ ID NO: 10). The a-p95-phosphoserine 343 antiserum was purified by affinity chromatography using phosphopeptide-conjugated Sepharose and antibody components directed against non-phosphospecific epitopes were removed on a Sepharose column conjugated with an unphosphorylated peptide (TPGPSLSQGVSVDE) (SEQ ID NO: 10). When used in Western blots, the antibody was pre-incubated with the unphosphorylated peptide to block any residual reactivity with unphosphorylated p95. The ATM monoclonal antibodies (D16.11 for immunoprecipitation, and D16.35 for immunoblotting ) are described above.

Plasmids and GST-fusion protein production. For GST fusion peptide expression vectors, complementary oligonucleotides encoding desired peptides (14 amino acids) were cloned into the BamHI/SmaI site of pGEX-2T (Pharmacia). The constructs were confirmed by restriction enzyme digests and DNA sequencing. To construct the larger GST-p95 (327–391) protein fragment, p95 DNA encoding amino acids 327–391 was amplified by PCR with Pfu polymerase using the following primers: 5' sense, 5'-TCCCCAGGAATTCCCGGCCATCCCAGTACAGGA-TTA-3' (SEQ ID NO:46), 3' antisense, 5'-TGCGGCCGCTCGAGTTTTTTGTTCCATTTTGGA-GAC-3' (SEQ ID NO:47). The amplified PCR product was digested with EcoRI /XhoI and was cloned into pGEX-4T-2 (Pharmacia). GST-p95 (327–391) S343A was generated using the QuikChange Site-Directed Mutagenesis kit (Stratagene). To construct the Myc-tagged p95 expression vector, the entire coding region of p95 was PCR- amplified with a pair of oligonucleotides:
5'-GAATCCCTCGAGCCTACCGCCATGTGGAAACTG-CTGCCCGCCGCG-3' (SEQ ID NO:48) and
5'-GTCGACGAGCGGCCGCCACCTCAGGGATCTTC-TCCTTTTTAAATAAGG-3' (SEQ ID NO:49). The PCR product was digested with XhoI/NotI and cloned into a pSG5 vector (Neupogen) that had a c-Myc tag inserted. The GST-peptides or fusion proteins were expressed in BL21 (DE)3 and purified on glutathione-Sepharose beads.

In vitro kinase assays and immunoprecipitation. In vitro kinase assays for wild-type and catalytically inactive ATM and ATR were performed as described above. Briefly, cell extracts were prepared from 293T cells which had been transfected with 10 mg of either ATM or ATR by resuspending cells in modified TGN buffer [50mM Tris (pH 7.5), 150niM NaCl, 1% Tween 20, 0.3% NP-40, 1 mM NaF, 1 mM Na$_3$VO$_4$, 1 mM PMSF, and 1x protease inhibitor mixture from Roche]. Cleared supernatants were immunoprecipitated with anti-Flag M2 antibody and protein A/G agarose, the beads were washed with TGN buffer followed by TGN buffer plus 0.5 M LiCl, and two washes with kinase buffer [20 mM HEPES (pH 7.5), 50 mM NaCl, 10 mM MgCl$_2$, 1 mM dithiothreitol (DTT) and 10 mM MnCl$_2$]. Finally, the immunoprecipitant was resuspended in 50 ml of kinase buffer containing 10 $\mu$Ci of [$\gamma$-$^{32}$p] ATP and 1 mg of GST-fusion substrate (GST-p53:1–101), in varying concentration of Mn$^{2+}$. The kinase reaction was conducted at 30° C. for 20 min and stopped by the addition of SDS-PAGE loading buffer. Proteins were separated on SDS-polyacrylamide gel electrophoresis (SDS-PAGE) and transferred to nitrocellulose. Radiolabeled proteins were visualized and quantitated on a Phosphorimager (Molecular Dynamics). Use of equivalent amounts of flag-tagged ATM or ATR in the different lanes was confirmed by immunoblotting with anti-flag antibody. In some reactions, either supercoiled DNA (pBluescript II KS, Stratagene) or linearized DNA (pBluescript II KS cut with EcoR1) was added (0, 0.2, 0.5, 1, and 2mg). For endogenous ATM kinase reactions, endogenous ATM was immunoprecipitated from GM0536 lymphhoblasts with ATM monoclonal antibody (D16.11) in M buffer (PBS, 10% glycerol, 0.2% Tween 20, 0.3% NP-40, 1 mM NaF, 1 mM Na$_3$VO$_4$, 1 mM PMSF, 1x protease inhibitor mixture]. After washing with M buffer and kinase buffer, in vitro kinase reactions were carried out according to procedures described above. The DNA-PK in vitro kinase reaction was performed as previously described (Gottlieb and Jackson, 1993), using 20 ng each of DNA-PKcs or DNA-PK (20 ng DNA-PKcs premixed with 20 ng Ku 70/80).

For immunoprecipation of p95 and ATM, 10$^6$ cells were harvested in lysis buffer [10 mM Tris HCl (pH 7.5), 200 mM NaCl, 5 mM EDTA, 0.5% NP-40]. After centrifugation, supernatants were incubated following standard protocols with either anti-p95 antibody or anti-ATM antibody. After extensive washing with a washing buffer [10 mM Tris HCl (pH 7.5), 100 mM NaCl, 5 mM EDTA, 0.5% NP-40], immunoprecipitants were analyzed by immunoblot. For lambda phosphatase treatment, immunoprecipitated p95 was washed with a phosphatase buffer and incubated with 400 units of lambda phosphatase at 30° C. for 30 min.

Phosphorylation of large GST-p95 protein fragment by ATM in vitro. Either GST-p95 (327–391) or GST-p95 (327–391) with serine at 343 substituted by alanine (S343A) was used as a substrate for ATM in vitro kinase reactions. Either transfected, flag-tagged wild-type (wt) or kinase-dead (kd) ATM or endogenous ATM from normal (WT; GM0536) or AT lymphoblasts (GM1526) was used as the source of ATM kinase. Flag-tagged ATM or endogenous ATM in each kinase reaction was blotted with anti-Flag or anti-ATM. The amount of phosphorylation of ATM and substrate was analyzed on a PhosphorImager.

In vivo phosphorylation of p95. Myc-tagged p95 (3 $\mu$g) was transiently co-transfected into 293T cells with wtATM, kdATM, or pCDNA3 (7$\mu$g) using calcium phosphate. After 2 days, cells were harvested and Myc-p95 was immunoprecipitated, subjected to SDS-PAGE (7.5%), transferred to nitrocelluose, and immunoblotted with $\alpha$-cMyc antibody or the $\alpha$-p95-phosphoserine 343 polyclonal mouse antibody. For metabolic labeling, the cells were washed with phosphate free RPMI plus 10% dialyzed fetal bovine serum and incubated for 30 min before irradiation. The cells were irradiated at 5 Gy and incubated with [32p] orthophosphate (1 $\mu$Ci/ml) for 30 min at 37° C. The labeled cells were lysed at 4° C. in TGN buffer and Myc-p95 and Flag-ATM were immunoprecipitated. After electrophoresis in 7.5% SDS-PAGE, radiolabeled p95 and ATM were visualized and quantified on a PhosphorImager.

Results

Cofactor requirements for ATM, ATR and DNA-PK. In order to elucidate potentially distinctive biochemical properties of the ATM, ATR, and DNA-PK kinases, we examined the cofactor requirements for their optimal activities. It had been previously reported that ATM and ATR required exogenous Mn$^{2+}$ for optimal in vitro kinase activity (Banin et al., Science, 281:1674, 1998; Caninan et al., Science, 281:1677, 1998). In contrast, DNA-PK has been reported to require Mg$^{2+}$ as well as the presence of DNA-ends and the DNA-binding proteins Ku70 and Ku80 for optimal activity (Gottlieb and Jackson, Cell, 72:131, 1993). However, since ATM specific activity increases in cells following exposure to ionizing radiation (Canman et al., supra, 1998) or introduction of double strand DNA breaks (Banin et al., supra, 1998), it was possible that ATM or ATR kinase activities are enhanced by the presence of DNA ends and that this dependence was being missed in our in vitro assays. For example, it was conceivable that the use of Mn$^{2+}$ in these assays decreased the dependence of ATM and ATR on DNA ends. Conversely, it was conceivable that the requirement of the use of DNA ends and/or Ku proteins in DNA-PK activity assays abrogated a need for Mn$^{2+}$ addition in these in vitro assays.

In order to test these possible scenarios, in vitro kinase assays with all three enzymes were performed using epitope-tagged ATM and ATR immunoprecipitated from transfected cells and biochemically purified DNA-PK as the kinase sources and GST-p53 (1–101) recombinant protein as a substrate. Kinase-inactive forms of ATM and ATR were used as controls in the assay to ensure that these activities were intrinsic. ATM and ATR kinases were dependent on the addition of exogenous Mn$^{2+}$, while DNA-PK activity was not altered by the addition of Mn$^{2+}$. The addition of supercoiled or linearized DNA to these reactions did not alter the activity of ATM or ATR, but consistent with previous observations (Gottlieb and Jackson, 1993), the dsDNA ends provided by linearized DNA significantly enhanced the activity of DNA-PK. The addition of either of these exogenous DNA sources did not relieve the dependence of ATM and ATR on exogenous Mn$^{2+}$.

It remained theoretically possible that these overexpressed ATM and ATR proteins had different cofactor requirements than would be seen for the normal endogenous proteins because of changes in molar ratios of ATM/ATR and cofactors. In addition, it was possible that immunoprecipitated ATM/ATR could be already contaminated with DNA or might have lost cofactors such as Ku proteins during immunoprecipitation. Therefore we re-examined both the Mn$^{2+}$ dependence and DNA-end dependence using endogenous ATM. In order to circumvent the concerns about potential loss of cofactors or prior DNA contamination, we also immunoprecipitated the endogenous ATM under very mild conditions without stringent washing (0.5M LiCl$_2$) and assessed the kinase activity either in the presence of added linearized DNA or with the addition of ethidium bromide, a DNA intercalator which is known to interfere with protein-DNA interaction (Schroter et al., EMBO. J., 4:3867, 1985; Lai and Herr, Proc. Natl. Acad. Sci. USA, 89:6958, 1992). The activity of endogenous ATM was still dependent on the addition of exogenous Mn$^{2+}$ and neither the exogenous addition of DNA ends nor the presence of ethidium bromide to inactivate potential contamination from endogenous DNA had any effect on its activity.

DNA-PK activity is enhanced by the presence of DNA ends via Ku-dependent association with the DNA and Mn$^{2+}$ is not required for its activity in in vitro kinase assay (Gottlieb and Jackson, supra, 1993). To further clarify potential distinctions between ATM/ATR and DNA-PK and to rule out the possibility that Mn$^{2+}$ might replace the requirement of DNA-PK activity for DNA ends or for the Ku70/80 cofactors, the in vitro activities of purified DNA-PKcs or DNA-PK holoenzyme containing Ku components were re-examined. Though DNA-PKcs alone has a basal level of activity toward GST-p53 (1–101), this activity was not enhanced by the addition of either $Mn^{2+}$ or DNA-ends. In contrast, the activity of the DNA-PK holoenzyme was remarkably enhanced by DNA-ends (approximately 10 times of basal level) and the addition of $Mn^{2+}$ had no effect on the DNA-PK activity either in the presence or absence of exogenous DNA. Thus, ATM and ATR kinases are distinguishable from DNA-PK in their lack of dependence on DNA-ends and their requirement for $Mn^{2+}$ for optimal activity.

Figure 1B:
Figure 1C:
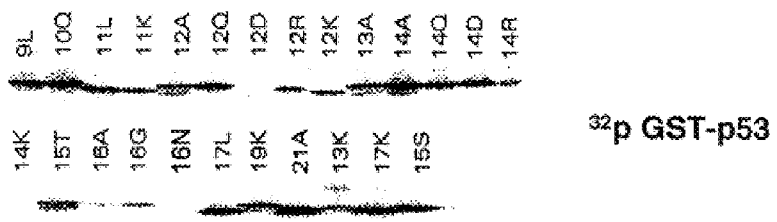

Consensus Sequence Elucidation via GST-p53 peptide mutagenesis analysis. Studies on other kinases have suggested that the nature and sequence of the amino acids surrounding the target phosphorylation site can play a critical role in modulating recognition of a substrate by a kinase (Pinna and Ruzzene, Biochim. Biophys. ACTA, 1314:191, 1996). We wished to clarify amino acids that affect the ability of ATM to phosphorylate a substrate and to use this information to try to identify other physiologic substrates. Short peptide sequences containing target amino acids have commonly been used as in vitro substrates for kinases. As described above, linkage of a short peptide sequence to a GST-tag provides a better in vitro substrate for ATM than a short peptide alone (presumably by increasing the size and secondary structure of the target peptide sequence). This approach also provided an easy way to generate and purify the peptide of interest. Thus, beginning with the known in vivo and in vitro target, serine 15 in p53, we attempted to determine which amino acids surrounding Ser15 in p53 were important modulators of phosphorylation by ATM. Wild type and mutated GST-conjugated p53 peptides containing 14 amino acids surrounding Ser15 were generated and used as in vitro kinase substrates for ATM, ATR and DNA-PK. Changes in some of the amino acids surrounding serine 15 had a dramatic effect on the ability of these kinases to phosphorylate the GST-p53 peptides, while others had little effect (FIGS. 1A–C). For example, peptides in which glutamine at position 16 was replaced with alanine, glycine, or arginine were very poor substrates for all three of these kinases. Thus, as has previously been reported for DNA-PK (Lees-Miller et al., Mol. Cell Biol., 12:5041, 1992), this result suggests that a glutamine adjacent to the target serine is also critical for substrate recognition by ATM and ATR. When the target serine at position 15 was mutated into threonine, the amount of phosphorylation was reduced to 13%, 53%, and 36% compared to the wild-type sequence for ATM, ATR, and DNA-PK, respectively. Thus, all three kinases appear to have a preference for phosphorylating serine over threonine. All three kinases poorly phosphorylated peptides with the substitutions 12D, 12R, 12K, 13K, 14K, and 14R, while the 12Q, 12A, 13A, 14A, 14Q, and 14D peptides were efficiently phosphorylated. These results indicate that hydrophobic amino acids at positions N-3 and N-1 and negatively charged amino acids at N-1 are positive determinants for substrate recognition by these kinases. In contrast, positively charged residues (11K, 12K, 12R, 13K, 14K, 14R, 17K, and 19K) around the SQ appear to have a significant negative influence on substrate phosphorylation.

Figure 2A:
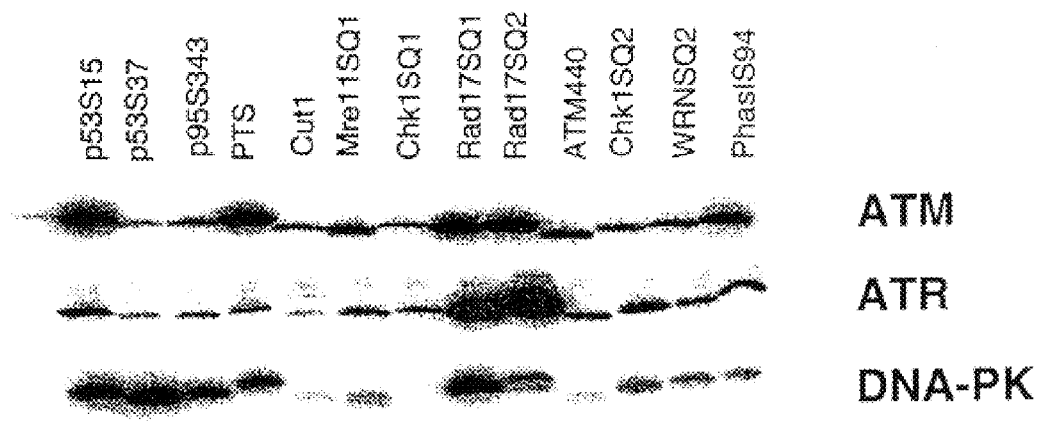
FIGS. 2A, 2B, and 2C. Phosphorylation of candidate targets of by ATM, ATR and DNA-PK in vitro. GST-peptides containing the putative target sequences were used as substrates for the kinase assay. The amino acid sequences of the GST-peptides are as indicated in Table 4.
Figure 2B:
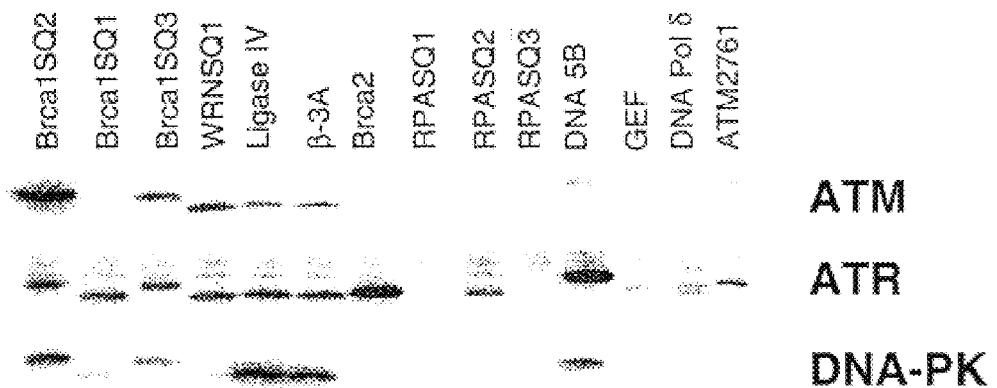
Figure 2C:
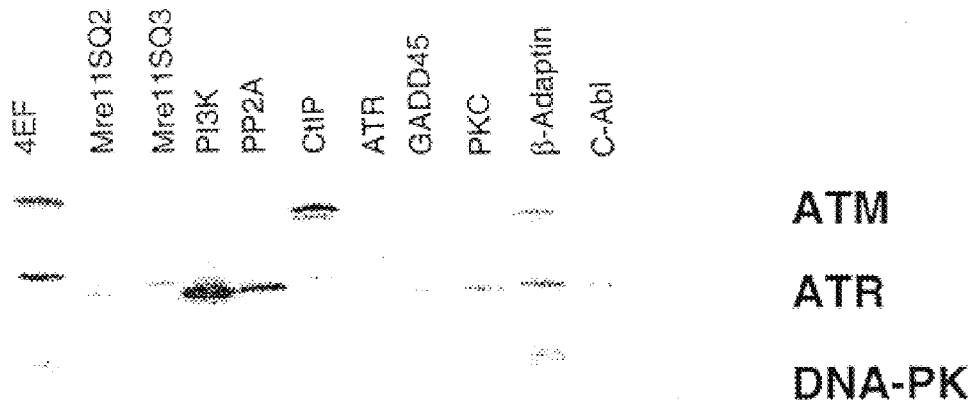

Though many of the amino acid substitutions had similar effects on all three of these kinases, some of the target manipulations resulted in differential effects. Peptides with 10Q, 17K, 17L substitutions remained relatively good substrates for ATM and ATR, but were very poor substrates for DNA-PK (FIG. 1). These observations suggest that the positions N-5 and N+2 are more important for substrate recognition by DNA-PK than for ATM and ATR. Most of the amino acid substitutions had similar effects on ATM and ATR, though the substitutions 12A, 13A, 14Q, and 14D appeared to result in differential quantitative effects on in vitro ATM and ATR activity (FIG. 1). One exception to this was the virtual abrogation of ATM activity by valine substitution for leucine at N-1 with no obvious affect on ATR activity (data not shown). Thus, ATM, but not ATR, may discriminate between valine and other hydrophobic amino acids at the position N-1. Further validation of this putative general consensus target sequence for ATM came from examination of a previously reported in vitro substrate for ATM, PhasI (Banin et al., supra, 1998). An amino acid sequence around Ser 94 in PhasI contains hydrophobic amino acids at N-3 and N-1 as well as an SQ motif. As predicted, a GST-Ser94 PhasI peptide proved to be an excellent in vitro substrate for ATM (FIG. 2).

Identification of new putative substrates of the ATM family. Using the preliminary consensus sequence generated from the p53 Ser15 peptide mutational analysis and the Ser94 sequence of PhasI, we searched a protein database for potential ATM substrates. Since the occurrence of this motif is not uncommon, many potential targets were identified. We initially evaluated the ability of ATM, ATR and DNA-PK to phosphorylate the peptide sequences of 36 proteins (Table 4), many of which were chosen because of potential physiological relevance to the AT phenotype. Only a fraction of the peptides tested were highly phosphorylated in vitro (FIG. 2). These included Rad17, p95, Brca1, PhasI, WRN, ser440 of ATM (ATM440, a potential autophosphorylation site), and a recently cloned sequence localized to an LOH site on chromosome 3p21.3 (which we call PTS for "putative tumor suppressor"). Since all of the tested peptides contained sequences which fit the general consensus derived from the mutational analysis above, other amino acid sequence determinants must also be involved in determining the substrate specificity for the ATM kinase and continued characterization of these substrates should allow further refinement of the recognition sequence.

TABLE 4

Amino acid sequences and relative phosphorylation by ATM kinase family members of the GST-peptides The sequences and accession numbers of the peptides studied are listed and the amounts of substrate phosphorylation relative to the p53ser15 site by each kinase is shown. nd = not determined.

| Accession Number | Protein Name | Test Peptide (Amino acid sequences) | SEQ ID NO. | Serine No. | Relative Phosphorylation (%) | | |
|---|---|---|---|---|---|---|---|
| | | | | | ATM | ATR | DNA-PK |
| p04637 | p53 | SVEPPLSQETFSDL | 7 | S15 | 100 | 100 | 100 |
| | p53 | VLSPLPSQAMDDLM | 8 | S37 | 9 | 31 | 132 |
| NP_004086 | 4EBP1 (Phas I) | EPPMEASQSHLRNS | 9 | S94 | 78 | 66 | 10 |

TABLE 4-continued

Amino acid sequences and relative phosphorylation by ATM kinase family members of the GST-peptides The sequences and accession numbers of the peptides studied are listed and the amounts of substrate phosphorylation relative to the p53ser15 site by each kinase is shown. nd = not determined.

| Accession Number | Protein Name | Test Peptide (Amino acid sequences) | SEQ ID NO. | Serine No. | Relative Phosphorylation (%) | | |
|---|---|---|---|---|---|---|---|
| | | | | | ATM | ATR | DNA-PK |
| NP_002476 | p95 | TPGPSLSQGVSVDE | 10 | S343 | 19 | 31 | 45 |
| p49959 | MRE11 (SQ1) | QQLFYISQPGSSVV | 11 | S264 | 20 | 48 | 10 |
| | MRE11 (SQ2) | FSVLRFSQKFVDRV | 12 | S386 | <1 | 17 | <1 |
| | MRE11 (SQ3) | RARALRSQSEESAS | 13 | S531 | <1 | 13 | <1 |
| | MRE11 (SQ4) | SASRGGSQRGRAFK | 14 | S590 | <1 | nd | nd |
| | MRE11 (SQ5) | SSSKIMSQSQVSKG | 15 | S648 | <1 | nd | nd |
| NP_001265 | CHK1 (SQ1) | NVKYSSSQPEPRTG | 16 | S317 | 14 | 58 | 2 |
| | CHK1 (SQ2) | VQGISFSQPTCPDH | 17 | S345 | 11 | 73 | 20 |
| AAC36334 | RAD17 (SQ1) | TWSLPLSQDSASEL | 18 | S646 | 81 | 733 | 97 |
| | RAD17 (SQ2) | ASELPASQPQPFSA | 19 | S656 | 91 | 1065 | 25 |
| AF091214 | WRN (SQ2) | TIGMHLSQAVKAGC | 20 | S1292 | 10 | 33 | 5 |
| | WRN (SQ1) | EKAYSSSQPVISAQ | 21 | S1141 | 25 | 49 | 14 |
| U76308 | ATR | TVEPIISQLVTVLL | 22 | S1333 | <1 | 10 | <1 |
| X164T6 | c-ABL | YPGIDLSQVYELLE | 23 | S446 | <1 | 8 | <1 |
| NP_000042 | ATM | PLLMILSQLLPQQR | 24 | S440 | 33 | 55 | 7 |
| | ATM | YKVVPLSQRSGVLE | 25 | S2761 | 3 | 22 | <1 |
| Z46973 | PI-3K | DLLMYLSQLVQALK | 26 | S397 | <1 | 150 | <1 |
| U64105 | p115-RhoGEF | RLRPLLSQLGGNSV | 27 | S899 | <1 | 15 | <1 |
| L13939 | β-ADAPTIN | CRAPEVSQHVYQAY | 28 | S935 | 5 | 22 | 2 |
| U43746 | BRCA2 | KVSPYLSQFQQDKQ | 29 | S2156 | <1 | 132 | <1 |
| M81735 | DNA POL-δ | LPCLEISQSVTGFG | 30 | S717 | <1 | 17 | <1 |
| U87269 | p120E4F | APEPPVSQELPCSR | 31 | S355 | 11 | 30 | 2 |
| U14680 | BRCA1 (SQ1) | SASLFSSQCSELED | 32 | S1298 | 2 | 38 | 6 |
| | BRCA1 (SQ2) | DCSGLSSQSDILTT | 33 | S1387 | 42 | 35 | 36 |
| | BRCA1 (SQ3) | SSEYPISQNPEGLS | 34 | S1466 | 8 | 33 | 12 |
| L07590 | PP2A (protein phosphatase 2A) | LLHIPVSQFKDADL | 35 | S61 | <1 | 34 | <1 |
| D79987 | CUT1 | GASPVLSQGVDPRS | 36 | S1615 | 9 | 20 | 5 |
| AF040703 | PTS (123F2) | WETPDLSQAEIEQK | 37 | S61 | 111 | 40 | 33 |
| X63071 | DNA 5B | QPEPPVSQSEISEP | 38 | S72 | 3 | 145 | 15 |
| X83441 | DNA LIG-IV | DLKLGVSQQTIFSV | 39 | S132 | 5 | 36 | 48 |
| U24186 | RPA34kD (SQ1) | FPAPAPSQAEKKSR | 40 | S33 | <1 | 5 | <1 |
| | RPA34kD (SQ2) | IVPCTISQLLSATL | 41 | S52 | <1 | 31 | <1 |
| | RPA34kD (SQ3) | TGNVEISQVTIVGI | 42 | S72 | <1 | 8 | <1 |
| L81504 | β3A Adaptin | ELKPVLSQG | 43 | S1092 | 6 | 22 | 44 |
| U72066 | CtIP | DPGADLSQYKMDVT | 44 | S664 | 12 | 12 | 2 |

We also tested the ability of DNA-PK and ATR to phosphorylate these GST-peptides and several distinctions between substrates recognized by these three kinases were apparent in the assays (FIG. 2). In general, ATM and ATR tended to recognize the same substrates, though quantitative differences were apparent in most cases. For example, even though ATR appears to be a much weaker kinase than ATM for most substrates tested (about 10–20 fold lower activity), ATR exhibited greater activity than ATM for two sites in Rad17 and also demonstrated good activity against sites from Brca2 and DNA-5B. The latter two peptides were very poor substrates for both ATM and DNA-PK and the second SQ in Rad17 was not a good substrate for DNA-PK (FIG. 2). Conversely, peptides containing sequences from ligase IV and the region surrounding Ser37 of p53 were highly phosphorylated by DNA-PK, but were not good substrates for ATM. From these approaches, we have developed a preliminary consensus target sequence which is recognized by ATM and we have identified a group of proteins containing good in vitro target sites for ATM which warrant further investigation as potential valid in vivo targets of ATM (Detailed Description, supra).

Structural factors present in a full-length protein, but absent in the GST-peptides we tested, could also influence the ability of ATM to phosphorylate a target protein. Thus, the next logical step in elucidating valid targets of the kinase was to test the ability of ATM to phosphorylate much larger peptides or full-length proteins from the putative target list. GST-linked peptides containing over 100 amino acids from the putative Rad7 (561–670) and Brca1SQ2 (1341–1440) sites were excellent in vitro substrates for ATM and ATR. In contrast, GST-WRN (1099–1198) and purified recombinant full-length WRN protein were not phosphorylated. A similar approach was used to evaluate the sequence in p95 (nibrin). A large GST-peptide containing serine 343 of p95 was an excellent in vitro substrate for ATM. Mutation of serine 343 to alanine in the target GST-p95 largely abrogated the ability of ATM to phosphorylate the protein, thus confirming this as an in vitro target site in the protein. These observations led to further investigation of p95, Rad17 and Brca1 (Example 4), but not WRN, as potential physiologic targets of ATM and ATR. The results with p95 and ATM are described below.

p95forms a complex with ATM and p95 phosphorylation after IR is not observed in AT cells. Because of the overlap of the physiologic abnormalities in AT and NBS (Nijmegen breakage syndrome), we were particularly interested in determining whether the p95 protein (nibrin), which is mutated in NBS, is a true physiologic target of ATM. Potential interactions between endogenous ATM and p95 proteins were initially evaluated by co-immunoprecipitation experiments using untreated and irradiated (10Gy, 1 hr) K562 cells, with detection of p95 and ATM by Western blotting. Anti-p95 antibodies brought down detectable amounts of ATM protein from cellular lysates, particularly after irradiation with no ATM detected using pre-immune serum (or no antibody) to precipitate. However, the reverse experiment using anti-ATM antibodies for the immunoprecipitation did not reveal detectable amounts of p95 immunoprecipitating with ATM. Similarly, we were unable to demonstrate co-immunoprecipitation of ATM and p95 after transient co-transfection. These results support the existence of physical interaction between ATM and p95 though it is likely to be weak and transient. However, it is not uncommon for kinase-substrate interactions to be relatively weak and transient. Thus, we remained interested in further examining the possibility that p95 is a physiologic substrate for ATM.

Figure 3:
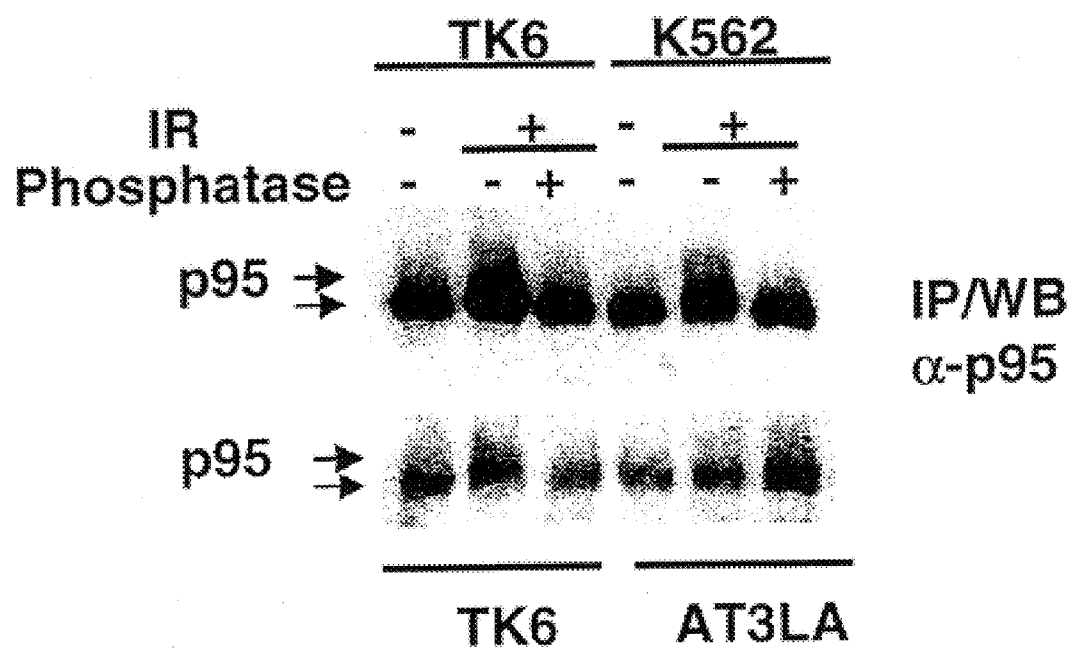
FIG. 3. p95 binds to ATM and IR induces phosphorylation of p95 in normal cells, resulting in mobility shift of p95 following IR in normal, but not AT, cells. Normal cells (TK6, K562) or AT cells (AT3LA) were treated with either 0 (−) or 10 (+) Gy irradiation and p95 was immunoprecipitated, either not treated (−) or treated (+) with lambda phosphatase, and analyzed by SDS-PAGE and western blotting for p95. The top arrowhead indicates the slower mobility band.

We observed a slower migration of p95 protein on SDS-PAGE after exposing two different mammalian cells to IR (FIG. 3). Since phosphatase treatment of the immunoprecipitated p95 eliminated this slowed migration (FIG. 3), it appeared that this altered migration represented an IR-induced phosphorylation of p95 protein. This concept was supported by the observation that metabolic labeling of 293T cells with $^{32}$p after co-transfection of epitope-tagged ATM (Ftg) and p95 (Myc) revealed a doubling of $^{32}$p incorporation into p95 after IR (5 Gy). In order to begin to evaluate the potential role of ATM in this IR-induced phosphorylation of p95, the IR-induced band shift was evaluated in AT cells. The altered p95 migration after IR failed to occur in AT cells (FIG. 3), thus implicating ATM in this phosphorylation event. However, demonstration of a direct phosphorylation of p95 by ATM after IR would require a more definitive approach.

Figure 4A:
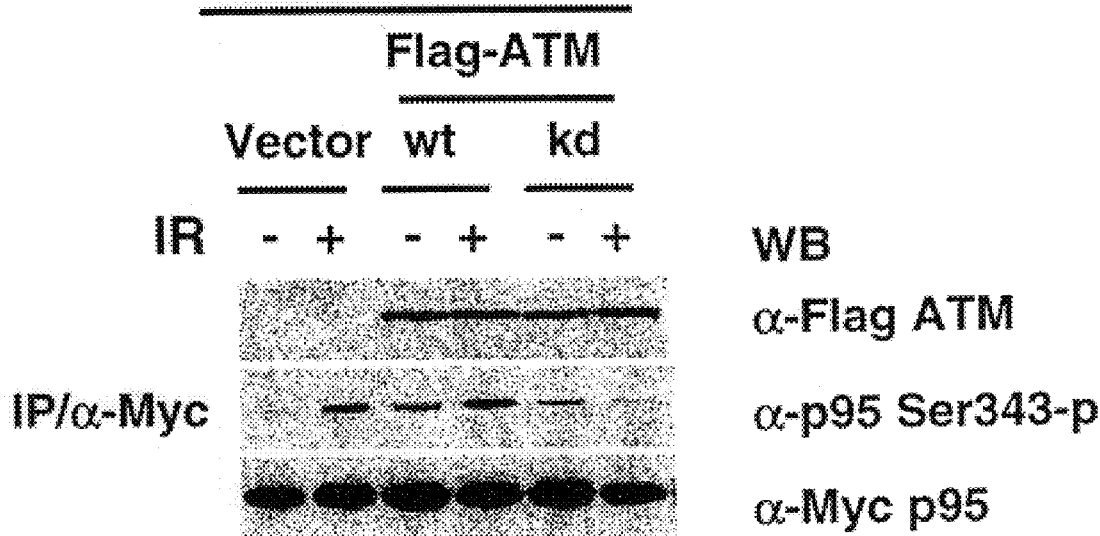
FIGS. 4A and 4B. In vivo phosphorylation of p95 on ser343 by ATM upon ionizing irradiation. (A) Phosphorylation of p95 on Ser343 by IR in an ATM-dependent manner in vivo. Myc-p95 was co-transfected into 293T cells with either empty vector or wild-type (wt) or kinase inactive (kd) Flag-ATM and cells were treated with either 0 (−) or 5 (+)

The phosphorylation of p95 on Ser343 is dependent on ATM and is defective in AT cells in response to ionizing radiation. In order to investigate whether ATM kinase phosphorylates p95 in response to IR and whether the site in p95 which gets phosphorylated by IR is the in vitro ATM target site in p95 that we had previously identified, we generated a polyclonal antibody which specifically recognizes p95 when it is phosphorylated at ser343 (as detected by blotting phosphorylated but not unphosphorylated 337–350 peptide containing phosphoserine or serine at position 343). The specificity of the antibody was illustrated by its ability to recognize the p95 peptide in its phosphorylated state, but not its unphosphorylated state, when incubated with blocking peptide. Using this antibody, we were able to ask whether IR induces phosphorylation of ser343 in p95 in vivo and whether this phosphorylation event is dependent on ATM. Either empty vector or wild-type or kinase-inactive (kd) forms of ATM were co-transfected into 293T cells along with myc-tagged p95 and radiation-induced phosphorylation of ser343 in p95 was examined. Immunoblots of immunoprecipitated p95 using the α-p95-phosphoserine-343 antibody revealed very low levels of p95ser343 phosphorylation in unirradiated cells and a dramatic increase in phosphorylation after IR (FIG. 4). Thus, serine 343 is at least one site in p95 which is phosphorylated in response to IR. Interestingly, when the kinase-inactive form of ATM was co-transfected with p95, it significantly inhibited this IR-induced phosphorylation of p95ser343 (FIG. 4). This suggests that similar to ATR (Cliby et al., EMBO. J., 17:159, 1998; Wright et al., Proc. Nat]. Acad. Sci. U.S. A, 95:7445, 1998; Tibbetts et al., Genes Dev., 13:152, 1999), overexpression of kinase-inactive ATM is functioning as a dominant-negative protein by inhibiting irradiation-induced p95 S343 phosphorylation by the endogenous ATM protein. (It is noted that overexpression of this kinase-inactive form of ATM exhibits dominant-negative activity in many other assays of ATM function as well.

Figure 4B:
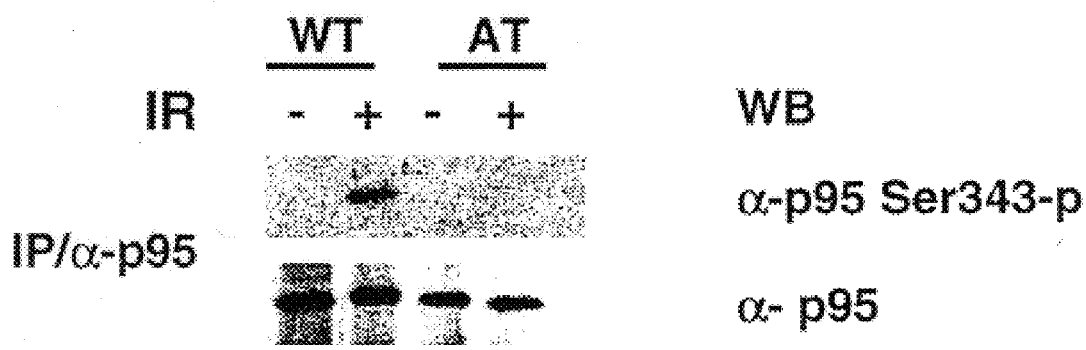

Thus, IR treatment of cells results in phosphorylation of the consensus ATM in vitro target site in p95 that we had previously identified and this IR-induced phosphorylation event is blocked by use of a dominant-negative form of ATM. As a final step in demonstrating a requirement for ATM kinase in the IR-induced p95ser343 phosphorylation, we examined the ser343 phosphorylation of endogenous p95 in response to DNA damage in normal and AT cells. Endogenous p95 was immunoprecipitated from unirradiated or irradiated normal (GM536) and AT lymphoblasts (GM1526) and subsequently examined by Western blotting with the anti-p95ser343 antibody. Phosphorylation of Ser343 of p95 was easily detected in irradiated cells containing wild-type ATM, but no reactivity with the phosphospecific antibody was detected in either unirradiated cells or AT cells with or without irradiation (FIG. 4B). Equivalent amounts of total immunoprecipitated p95 protein were present under all conditions. These results demonstrated that p95 protein is phosphorylated on ser343 in an ATM-dependent manner in response to ionizing radiation.

Experiments have confirmed the physiological relevance of ATM phosphorylation of p95. Overexpression of cDNA for a mutant form of p95 at the ATM phosphorylation site (Ser 343→Ala) altered the radiation response of the cells.

Discussion

Identification of physiologic substrates for cellular kinases is a daunting, but critically important, aspect of understanding biological processes. It had previously been demonstrated that p53 protein is a physiologic target of the ATM kinase (Banin et al., supra, 1998; Canman et al., supra, 1998), but most of the physiologic abnormalities in AT patients and AT cells are not attributable to defects in signaling to p53. Thus, it is clear that there must be other physiologic targets of this kinase. Building upon the assay described above (Example 2; Canman et al., supra, 1998), we clarified the optimal conditions for in vitro measurements of ATM kinase activity. These experiments demonstrated significant differences in the co-factor requirements of ATM and ATR compared to the related kinase, DNA-PK. In particular, ATM and ATR require $Mn^{2+}$, but not DNA ends or Ku proteins, for optimal in v ends, and Ku proteins. Optimization of in vitro conditions to evaluate these three kinases allows us to then use these in vitro assays for screening of potential physiologic targets of these enzymes.

Our general approach was to first identify peptide sequences recognized by these kinases in vitro, then extend these observations to full-length proteins, followed by investigation of putative targets in vivo. There are several advantages to this approach. First, it appears that the GST-peptides are much better than small synthetic peptides as in vitro substrates and it is easier and cheaper to make the oligonucleotides and clone them into the GST plasmid than to synthesize every peptide of interest. Second, easy alteration of the sequence of the oligonucleotides attached to the GST-linker allows us to quickly and easily define a general consensus target motif and simultaneously identify the putative phosphorylation site for each target. The advantage of immediately knowing the potential site of phosphorylation is exemplified by how quickly it allowed us to identify p95 as a true physiologic substrate after the in vitro work had identified ser343 of p95 as the likely target site and justified the effort required to make a site-specific, phosphoserine-specific antibody.

Third, comparing the abilities of the three related kinases to phosphorylate each of these substrates in vitro provides unexpected clues about how they differ in in vivo function and provides distinctions between the enzymes for development of specific inhibitors of these kinases. As examples of insights that were not predictable a priori, our in vitro data suggests that Rad 17 may be a physiologic substrate for ATR and not DNA-PK and that ligase IV may be a physiologic substrate for DNA-PK and not ATM or ATR. This latter possibility is particularly intriguing because of the recently described role for ligase IV in V(D)J recombination events that also involve DNA-PK (Frank et al., Nature, 396:173, 1998). Building upon the preliminary consensus target sequence for ATM generated from the p53ser15 mutagenesis work, we were then able to identify some new potential substrates for ATM, ATR and DNA-PK including Rad17, Brca1, Brca2 p95, PTS, PhasI, WRN, DNA-5B, and Ligase IV. These targets represented the first screen of potential substrates and additional proteins with reasonable ATM target sites are continuing to be evaluated.

It should be noted that the consensus target sequences we characterized should be considered as guidelines rather than concrete rules. However, it does appear that glutamine at position N+1 appears is absolutely required for activity of this kinase family and that nearby hydrophobic amino acids, especially at positions N−3 and N−1, are important determinants. It is noted that since substitution of threonine for serine had only a quantitative effect on phosphorylation by all three enzymes, it is entirely conceivable that threonine could replace serine as the targeted amino acid in certain protein targets.

ATM, p95 and other potential substrates. AT, with mutations in the ATM gene, and NBS, with mutations in the p95/nibrin gene, share many phenotypic abnormalities, including chromosomal instability, radiation sensitivity and defects in cell cycle checkpoints in response to IR (Shiloh, Ann. Rev. Genet., 31:635, 1997; Featherstone and Jackson, Curr. Biol., 8:R622, 1998). Thus, it was reasonable to suspect that p95 and ATM might be involved in similar cellular processes in response to DNA damage responses and provided justification for choosing this putative ATM target as the initial protein suggested by our in vitro screen to characterize in vivo. This Example shows that ATM phosphorylates p95 on ser343 in vitro, that ATM can bind to p95 in cells and that the phosphorylation of p95 in vivo in response to IR occurs on ser343 in an ATM-dependent manner. This set of observations is identical to those used to conclude that ATM is required for phosphorylating ser15 of p53 in response to IR (Banin et al., supra, 1998; Canman et al., supra, 1998).

At present, we do not know the functional significance of this ATM phosphorylation of p95Ser343 in response to IR. However, this physiologic linkage may in part explain how mutations in either the ATM or p95/nibrin genes result in similar, though not identical, phenotypes. p95 associates with hRad50 and hMre1, and this complex has been implicated in the recognition of DNA double strand breaks as well as the repair of DNA double strand breaks (Carney et al., Cell, 93:477, 1998; Varon et al., Cell, 93:467, 1998; Nelms et al., Science, 280:590, 1998; Trujillo et al., J. Biol. Chem., 273:21447, 1998; Paul and Gellert, Genes Dev., 13:1276, 1999). The corresponding protein complex in Saccharomyces cerevisiae, containing ScRad50, ScMre11, and ScXRS2, plays important roles in recombinational repair, meiotic recombination and telomere maintenance (Fabre et al., Mol. Gen. Genet., 195:139, 1984; Ivanov et al., Genetics, 132:651, 1992; Johzuka and Ogawa, Genetics, 139:1521, 1995; Tsukamoto et al., Genetics, 142:383, 1996; Moore and Haber, Mol. Cell Biol., 16:2164, 1996; Ohta et al., Proc. Natl. Acad. Sci USA, 95:646, 1998; Haber, Cell, 95:583, 1998; Usui et al., Cell, 95:705, 1998; Chamankhah and Xiao, Nucl. Acids Res., 27:20729, 1999). Complexes of hMre11, Rad50, and p95 relocalize to DNA strand break regions within 30 min after exposure of mammalian cells to IR, presumably to recognize the DNA damage (Nelms et al., supra, 1998), and form nuclear foci at 6 to 8 hours later, perhaps to facilitate DNA repair (Maser et al., Mol. Cell Biol., 17:6087, 1997; Carney et al., supra, 1998). Interestingly, the formation of these foci is defective in NBS cells and has been reported to be measurably reduced in AT cells (Maser et al., supra, 1997). These observations suggest that p95 is likely to be required for the localization of the hMre11/hRad50 complex to DNA damage-induced breaks and that ATM dysfunction might alter the rate of the formation or stability of the hMre11/hRad50/p95 foci in response to IR. Our observations suggest that the link of ATM to this process may be through phosphorylation of p95 on Ser343. The ATM target site in p95, Ser343, is immediately adjacent to the BRCT domain in the N-terminal portion of p95, which is believed to be involved in protein-protein interaction (Critchlow et al., Curr. Biol., 7:588, 1997; Saka et al., Genes Dev., 11:3387, 1997; Yu et al., J. Biol. Chem., 273:25388, 1998; Li et al., Oncogene, 18:1689, 1999; Soulier and Lowndes, Curr. Biol., 9:551, 1999). Thus, it is also possible that phosphorylation of p95 on ser343 by ATM affects its interaction with other proteins A direct role for ATM in repair of DNA breaks has been difficult to clarify. Measurements of religation of DNA breaks in AT cells after IR is not reproducibly abnormal (McKinnon, Hum. Genet., 75:197, 1987) nor is there an obvious DSB repair deficiency in NBS cells (Nove et al., Mutat. Res., 163:225, 1986; Kraakman-van der Zwet et al., Mutat. Res., 434:17, 1999). However, many of the phenotypic abnormalities in A-T cells and NBS cells clearly indicate a problem with response to DNA breaks. These abnormalities include a high frequency of chromosomal translocations or inversions involving chromosomes 7 and 14 in T-cells (which contain sites of V(D)J recombination), increased telomere fusions and accelerated telomere shortening, high numbers of chromosomal gaps and breaks after IR, defects in meiotic recombination, and radiation sensitivity (Lavin and Shiloh, Ann. Rev. Immunol., 15:177, 1997; Shiloh, Ann. Rev. Genet., 31:635, 1997). The observation that ATM phosphorylates p95 in response to ionizing radiation now demonstrates that these proteins function in the same DNA damage response pathway.

Other potential targets that we identified in our screens could uncover other roles for ATM in DNA repair processes. Patients with heterozygous germline mutations in the BRCA1 gene have a markedly increased risk of developing breast cancer (Futreal et al., Science, 266:120, 1994; Miki et al., Science, 266:66, 1994) and it has been suggested that heterozygous germline ATM mutations also increase breast cancer risk (Swift et al., N. Engl. J. Med., 316:1289, 1987; Swift et al., N. Engl. J. Med., 325:1831, 1991; Lavin, BMJ, 3 71:486, 1998; Swift and Su, BMJ, 318:400, 1999). Additionally, it appears that Brca1 participates both in transcription as a transcription factor and DNA-repair through association with Rad51/Brca2 (Scully et al., Cell, 88:265, 1997; Somasundaram et al., Nature, 389:187, 1997; Chen et al., Mol. Cell, 2:317, 1998). Using an approach similar to that used for p95, further studies can investigate the degree to which Brca1 is an in vivo target of ATM and the physiologic significance of such a phosphorylation.

The function of the mammalian Rad17 protein is currently unknown, but data from yeast implicate this protein in DNA damage checkpoint control (Bao et al., Cell Growth Differ., 9:961, 1998; Bluyssen et al., Genomics, 55:219, 1999; Li et al., supra, 1999). Elucidation of the extent to which this is a physiologic target of either the ATM or ATR kinases may shed additional light on regulation of mammalian DNA repair processes.

Finally, since ATM kinase activity is enhanced by DNA breakage (Banin et al., supra, 1998; Canman et al., supra, 1998), it appears that the potential ATM autophosphorylation site (ATM440) identified herein contributes to regulation of its activity. The studies provide initial insights into understanding AT and signaling pathways involving ATM and provide a paradigm for further studies of this kinase family and potentially other kinases.

Example 4
Identification of Brca1 as an In vitro ATM Target

Taking similar approaches to that of Example 3 with a number of other proteins has yielded preliminary data showing that the breast cancer susceptibility gene product, Brca1, is also a physiologic target of the ATM kinase. All of the potential ATM target sites (based on our consensus sequence) in Brca1 were tested and the data suggest that there are two sites in Brca1 phosphorylated by ATM. The results have potential significance for both cancer causation and new cancer therapeutic approaches.

Example 5
Role of ATM in Insulin Signaling

We have further investigated the role of ATM in insulin signaling. As discussed above, ATM appears to be critical for insulin signaling in adipocytes. Experimental evidence supports this. First, PhasI/4E-BP1 (but not 4E-BP2) is a good substrate for ATM, and its phosphorylation site has been mapped. As shown in Example 3, serine 94 of human PhasI/4E-BP1 (equivalent to serine 93 of rat PhasI/4E-BP1) is a good in vitro peptide substrate for ATM. However, unexpectedly, ATM is able to phosphorylate full-length 4E-BP1 mutated at serine 94, thus suggesting that another amino acid is a relevant target in the full-length protein. Using the ATM target consensus, we identified another potential ATM phosphorylation site in 4E-BP1 and then showed that ATM actually phosphorylates serine 111 of the protein.

In vitro kinase assays were used to show that ATM is capable of phosphorylating GST-petides containing either an 18 amino acid region of the protein around serine 93 or around serine 111 of 4E-BP1. ATM can phosphorylate full-length 4E-BP 1 as well as 4E-BP1 mutated at serine 93, but cannot phosphorylate 4E-BP1 mutated at serine 111. This demonstrates that serine 111 is the site of phosphorylation by ATM in 4E-BP1.

A recent manuscript identified serine 111 of 4E-BP1 as an important insulin-induced in vivo phosphorylation site in adipocytes (Hessom, et al., Journal of Biochemistry, 336:39–48, 1998), which lends further importance to this observation. We have since extended these observations to demonstrate that insulin treatment of adipocytes directly activates the ATM kinase (FIG. 3).

ATM was immunoprecipitated from 3T3-L1 after differentiation and without (−) or with (+) exposure to insulin. The immunoprecipitated ATM was then used in an in vitro kinase assay with GST-4E-BP1 protein as the substrate. Equivalent amounts of ATM and GST-4E-BP1 were used. Insulin treatment significantly enhanced ATM kinase activity in these differentiated cells, when normalized to standards for the amount of 4E-BP1 protein.

Further data demonstrated the physiologic importance of this process by showing that ATM activity is necessary for insulin induced release of 4E-BP1 from eIF-4E. Fibroblasts from normal or AT mice were treated with (+) or without (−) insulin and total cellular and complexed eIF-4E and 4E-BP1 were examined by Western blot. Total cellular eIF-4E and 4E-BP1 were unchanged by insulin treatment. The amount of 4E-BP1 bound to eIF-4E was examined by immunoprecipitating eIF-4E with a methyl-G column and then blotting for both proteins. Insulin caused a release of 4E-BP1 from eIF-4E in normal cells (A29), but much less 4E-BP1 was released in AT cells (A38). This result was repeated in human fibroblasts expressing a dominant-negative form of ATM.

Finally, we also showed that mutation of the ATM target site in 4E-BP1, serine 111, also abrogates insulin-mediated release of 4E-BP1 from eIF-4E. This release of 4E-BP1 is considered necessary for insulin stimulation of adipocyte growth.

Thus, these observations provide further significant evidence supporting the role of ATM in insulin signaling in adipocytes and the potential utility of ATM inhibition in the treatment of obesity. Furthermore, it illustrates yet another example of how the in vitro screening assay and clarification of a consensus target sequence for ATM of this invention provide critical biological insights.

Example 6
IGF-I Activates ATM

Since the growth factor and survival factor insulin-like growth factor (IGF)-I activates cellular signaling in a manner similar to insulin, the insulin observations above led us to also investigate whether IGF-I might activate ATM kinase. Since IGF-I is a neuronal survival factor and since patients with mutated ATM exhibit neuronal degeneration, we were particularly intrigued by the possibility that ATM activation by IGF-I might be cell-type specific. Previous results demonstrated that the neuroblastoma cell line, SY5Y, responds to IGF-I, and this cell line can be differentiated along a neuronal lineage in in vitro culture with retinoic acid. Undifferentiated and differentiated SY5Y cells were treated with IGF-I and ATM activation was assessed.

ATM was immunoprecipitated from either undifferentiated or differentiated SY5Y neuroblastoma cells after treatment with 10nM IGF-I (control cells were untreated). The immunoprecipitated ATM was then used in an in vitro kinase assay with the GST-p53 protein as the substrate. Equivalent amounts of ATM and GST-p53 were used. IGF-I treatment significantly enhanced ATM kinase activity in the differentiated, but not undifferentiated, cells.

This observation, derived from the technologies described above, provides new insights into a novel mechanism of neurodegeneration. We can now identify the physiologic substrates of the ATM kinase in this setting using the in vitro assays and consensus sequence and then follow up in vitro leads with in vivo studies, as with the p95/nibrin target described above (Example 3).

Example 7
Use of the ATM Kinase Assay for Identification of an ATM Inhibitor

A useful application of the in vitro assay for ATM kinase activity disclosed herein is for screening compounds which inhibit ATM kinase activity. Such compounds would then be candidate compounds for radiosensitization of tumors in vivo. The in vitro assay described above (Example 1) utilizes the recombinant ATM kinase protein (usually with an epitope-tag for ease of purification) and an identified substrate, such as the sequence in the amino-terminal domain of p53 protein. Adding a compound that is a candidate inhibitor blocks or significantly reduces (compared to the control level of phosphorylation without the candidate inhibitor) the ability of the recombinant ATM protein to phosphorylate this substrate in this assay. The readout for the level of ATM-mediated phosphorylation may be incorporation of radioactive phosphate, though other options for readouts of kinase activity are also available. Development of this type of in vitro assay is particularly convenient for drug screens because it can be set up in automated high throughput screening assays. For example, the substrate can be attached to wells in microtiter dishes. Recombinant ATM enzyme can be added to the wells with appropriate buffers and co-factors for kinase reaction, and candidate inhibitory compounds can be added to selected wells to evaluate ones which inhibit the kinase activity. As a further control, kinase-dead ATM protein can be added to certain wells to further demonstrate specificity in these assays. Use of the identified optimal peptide consensus sites as targets for ATM activity can further enhance the sensitivity and specificity of the assay. In addition, if small peptides by themselves (rather than as GST-conjugated peptides) are successfully used in this assay, then the ability to utilize this drug screening approach on a large scale is further enhanced because the peptide substrate can be made synthetically rather than by recombinant methods.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values are approximate, and are provided for description.

All patents, patent applications, publications, and other materials cited herein are hereby incorporated herein reference in their entireties.

What is claimed is:

1. A method for identifying an inhibitor of ATM-mediated kinase activity comprising determining the extent of HTLV integration in the presence of apotential inhibitor of ATM-mediated kinase activity, wherein the absence of HTLV integration indicates that said potential inhibitor is an inhibitor of ATM-mediated kinase activity.

2. The method of claim 1, wherein the extent of HTLV integration is determined by determining the extent of cell survival after HTLV infection.

* * * * *

UNITED STATES PATENT AND TRADEMARK OFFICE
CERTIFICATE OF CORRECTION

PATENT NO. : 6,348,311 B1 Page 1 of 1
DATED : February 19, 2002
INVENTOR(S) : Kastan, Canman, Kim and Lim It is certified that error appears in the above-identified patent and that said Letters Patent is hereby corrected as shown below:

<u>Title page,</u>
Item [73], Assignees, delete "St. Jude Childre's Research Hospital," and substitute
-- St. Jude Children's Research Hospital, --

Signed and Sealed this

Sixth Day of August, 2002

Attest:

JAMES E. ROGAN
Attesting Officer    Director of the United States Patent and Trademark Office

SEQUENCE LISTING

```
<160> NUMBER OF SEQ ID NOS:  49

<210> SEQ ID NO 1
<211> LENGTH: 7
<212> TYPE: PRT
<213> ORGANISM: Artificial Sequence
<220> FEATURE:
<221> NAME/KEY: PHOSPHORYLATION
<222> LOCATION: 4
<223> OTHER INFORMATION: Artificial sequence is a synthetic sequence.
      Xaa at position one is a hydrophobic amino acid.
      Xaa at position three is a hydrophobic amino acid or Asp.
      Xaa at positions two, six, and seven is any amino acid.

<400> SEQUENCE: 1

Xaa Xaa Xaa Ser Gln Xaa Xaa
1               5

<210> SEQ ID NO 2
<211> LENGTH: 7
<212> TYPE: PRT
<213> ORGANISM: Artificial Sequence
<220> FEATURE:
<221> NAME/KEY: PHOSPHORYLATION
<222> LOCATION: 4
<223> OTHER INFORMATION: Artificial sequence is a synthetic sequence.
      Xaa at position seven is any amino acid.

<400> SEQUENCE: 2

Pro Pro Asp Ser Gln Glu Xaa
1               5

<210> SEQ ID NO 3
<211> LENGTH: 7
<212> TYPE: PRT
<213> ORGANISM: Artificial Sequence
<220> FEATURE:
<221> NAME/KEY: PHOSPHORYLATION
<222> LOCATION: 4
<223> OTHER INFORMATION: Artificial sequence is a synthetic sequence.
      Xaa at position seven is any amino acid.
```

```
<400> SEQUENCE: 3

Leu Pro Leu Ser Gln Asp Xaa
 1               5

<210> SEQ ID NO 4
<211> LENGTH: 7
<212> TYPE: PRT
<213> ORGANISM: Artificial Sequence
<220> FEATURE:
<221> NAME/KEY: PHOSPHORYLATION
<222> LOCATION: 4
<223> OTHER INFORMATION: Artificial sequence is a synthetic sequence.
      Xaa at position seven is any amino acid.

<400> SEQUENCE: 4

Leu Pro Leu Ser Gln Pro Xaa
 1               5

<210> SEQ ID NO 5
<211> LENGTH: 7
<212> TYPE: PRT
<213> ORGANISM: Artificial Sequence
<220> FEATURE:
<221> NAME/KEY: PHOSPHORYLATION
<222> LOCATION: 4
<223> OTHER INFORMATION: Artificial sequence is a synthetic sequence.
      Xaa at position seven is any amino acid.

<400> SEQUENCE: 5

Leu Pro Ala Ser Gln Asp Xaa
 1               5

<210> SEQ ID NO 6
<211> LENGTH: 7
<212> TYPE: PRT
<213> ORGANISM: Artificial Sequence
<220> FEATURE:
<221> NAME/KEY: PHOSPHORYLATION
<222> LOCATION: 4
<223> OTHER INFORMATION: Artificial sequence is a synthetic sequence.
      Xaa at position seven is any amino acid.

<400> SEQUENCE: 6

Leu Pro Ala Ser Gln Pro Xaa
 1               5

<210> SEQ ID NO 7
<211> LENGTH: 14
<212> TYPE: PRT
<213> ORGANISM: Homo sapiens

<400> SEQUENCE: 7

Ser Val Glu Pro Pro Leu Ser Gln Glu Thr Phe Ser Asp Leu
 1               5                  10

<210> SEQ ID NO 8
<211> LENGTH: 14
<212> TYPE: PRT
<213> ORGANISM: Homo sapiens

<400> SEQUENCE: 8

Val Leu Ser Pro Leu Pro Ser Gln Ala Met Asp Asp Leu Met
 1               5                  10

<210> SEQ ID NO 9
<211> LENGTH: 14
<212> TYPE: PRT
```

<213> ORGANISM: Homo sapiens

<400> SEQUENCE: 9

Glu Pro Pro Met Glu Ala Ser Gln Ser His Leu Arg Asn Ser
1               5                   10

<210> SEQ ID NO 10
<211> LENGTH: 14
<212> TYPE: PRT
<213> ORGANISM: Homo sapiens

<400> SEQUENCE: 10

Thr Pro Gly Pro Ser Leu Ser Gln Gly Val Ser Val Asp Glu
1               5                   10

<210> SEQ ID NO 11
<211> LENGTH: 14
<212> TYPE: PRT
<213> ORGANISM: Homo sapiens

<400> SEQUENCE: 11

Gln Gln Leu Phe Tyr Ile Ser Gln Pro Gly Ser Ser Val Val
1               5                   10

<210> SEQ ID NO 12
<211> LENGTH: 14
<212> TYPE: PRT
<213> ORGANISM: Homo sapiens

<400> SEQUENCE: 12

Phe Ser Val Leu Arg Phe Ser Gln Lys Phe Val Asp Arg Val
1               5                   10

<210> SEQ ID NO 13
<211> LENGTH: 14
<212> TYPE: PRT
<213> ORGANISM: Homo sapiens

<400> SEQUENCE: 13

Arg Ala Arg Ala Leu Arg Ser Gln Ser Glu Glu Ser Ala Ser
1               5                   10

<210> SEQ ID NO 14
<211> LENGTH: 14
<212> TYPE: PRT
<213> ORGANISM: Homo sapiens

<400> SEQUENCE: 14

Ser Ala Ser Arg Gly Gly Ser Gln Arg Gly Arg Ala Phe Lys
1               5                   10

<210> SEQ ID NO 15
<211> LENGTH: 14
<212> TYPE: PRT
<213> ORGANISM: Homo sapiens

<400> SEQUENCE: 15

Ser Ser Ser Lys Ile Met Ser Gln Ser Gln Val Ser Lys Gly
1               5                   10

<210> SEQ ID NO 16
<211> LENGTH: 14
<212> TYPE: PRT
<213> ORGANISM: Homo sapiens

```
<400> SEQUENCE: 16

Asn Val Lys Tyr Ser Ser Gln Pro Glu Pro Arg Thr Gly
 1               5                  10

<210> SEQ ID NO 17
<211> LENGTH: 14
<212> TYPE: PRT
<213> ORGANISM: Homo sapiens

<400> SEQUENCE: 17

Val Gln Gly Ile Ser Phe Ser Gln Pro Thr Cys Pro Asp His
 1               5                  10

<210> SEQ ID NO 18
<211> LENGTH: 14
<212> TYPE: PRT
<213> ORGANISM: Homo sapiens

<400> SEQUENCE: 18

Thr Trp Ser Leu Pro Leu Ser Gln Asp Ser Ala Ser Glu Leu
 1               5                  10

<210> SEQ ID NO 19
<211> LENGTH: 14
<212> TYPE: PRT
<213> ORGANISM: Homo sapiens

<400> SEQUENCE: 19

Ala Ser Glu Leu Pro Ala Ser Gln Pro Gln Pro Phe Ser Ala
 1               5                  10

<210> SEQ ID NO 20
<211> LENGTH: 14
<212> TYPE: PRT
<213> ORGANISM: Homo sapiens

<400> SEQUENCE: 20

Thr Ile Gly Met His Leu Ser Gln Ala Val Lys Ala Gly Cys
 1               5                  10

<210> SEQ ID NO 21
<211> LENGTH: 14
<212> TYPE: PRT
<213> ORGANISM: Homo sapiens

<400> SEQUENCE: 21

Glu Lys Ala Tyr Ser Ser Ser Gln Pro Val Ile Ser Ala Gln
 1               5                  10

<210> SEQ ID NO 22
<211> LENGTH: 14
<212> TYPE: PRT
<213> ORGANISM: Homo sapiens

<400> SEQUENCE: 22

Thr Val Glu Pro Ile Ile Ser Gln Leu Val Thr Val Leu Leu
 1               5                  10

<210> SEQ ID NO 23
<211> LENGTH: 14
<212> TYPE: PRT
<213> ORGANISM: Homo sapiens

<400> SEQUENCE: 23
```

```
Tyr Pro Gly Ile Asp Leu Ser Gln Val Tyr Glu Leu Leu Glu
 1               5                  10
```

<210> SEQ ID NO 24
<211> LENGTH: 14
<212> TYPE: PRT
<213> ORGANISM: Homo sapiens

<400> SEQUENCE: 24

```
Pro Leu Leu Met Ile Leu Ser Gln Leu Leu Pro Gln Gln Arg
 1               5                  10
```

<210> SEQ ID NO 25
<211> LENGTH: 14
<212> TYPE: PRT
<213> ORGANISM: Homo sapiens

<400> SEQUENCE: 25

```
Tyr Lys Val Val Pro Leu Ser Gln Arg Ser Gly Val Leu Glu
 1               5                  10
```

<210> SEQ ID NO 26
<211> LENGTH: 14
<212> TYPE: PRT
<213> ORGANISM: Homo sapiens

<400> SEQUENCE: 26

```
Asp Leu Leu Met Tyr Leu Ser Gln Leu Val Gln Ala Leu Lys
 1               5                  10
```

<210> SEQ ID NO 27
<211> LENGTH: 14
<212> TYPE: PRT
<213> ORGANISM: Homo sapiens

<400> SEQUENCE: 27

```
Arg Leu Arg Pro Leu Leu Ser Gln Leu Gly Gly Asn Ser Val
 1               5                  10
```

<210> SEQ ID NO 28
<211> LENGTH: 14
<212> TYPE: PRT
<213> ORGANISM: Homo sapiens

<400> SEQUENCE: 28

```
Cys Arg Ala Pro Glu Val Ser Gln His Val Tyr Gln Ala Tyr
 1               5                  10
```

<210> SEQ ID NO 29
<211> LENGTH: 14
<212> TYPE: PRT
<213> ORGANISM: Homo sapiens

<400> SEQUENCE: 29

```
Lys Val Ser Pro Tyr Leu Ser Gln Phe Gln Gln Asp Lys Gln
 1               5                  10
```

<210> SEQ ID NO 30
<211> LENGTH: 14
<212> TYPE: PRT
<213> ORGANISM: Homo sapiens

<400> SEQUENCE: 30

```
Leu Pro Cys Leu Glu Ile Ser Gln Ser Val Thr Gly Phe Gly
 1               5                  10
```

<210> SEQ ID NO 31
<211> LENGTH: 14
<212> TYPE: PRT
<213> ORGANISM: Homo sapiens

<400> SEQUENCE: 31

Ala Pro Glu Pro Pro Val Ser Gln Glu Leu Pro Cys Ser Arg
1               5                   10

<210> SEQ ID NO 32
<211> LENGTH: 14
<212> TYPE: PRT
<213> ORGANISM: Homo sapiens

<400> SEQUENCE: 32

Ser Ala Ser Leu Phe Ser Ser Gln Cys Ser Glu Leu Glu Asp
1               5                   10

<210> SEQ ID NO 33
<211> LENGTH: 14
<212> TYPE: PRT
<213> ORGANISM: Homo sapiens

<400> SEQUENCE: 33

Asp Cys Ser Gly Leu Ser Ser Gln Ser Asp Ile Leu Thr Thr
1               5                   10

<210> SEQ ID NO 34
<211> LENGTH: 14
<212> TYPE: PRT
<213> ORGANISM: Homo sapiens

<400> SEQUENCE: 34

Ser Ser Glu Tyr Pro Ile Ser Gln Asn Pro Glu Gly Leu Ser
1               5                   10

<210> SEQ ID NO 35
<211> LENGTH: 14
<212> TYPE: PRT
<213> ORGANISM: Homo sapiens

<400> SEQUENCE: 35

Leu Leu His Ile Pro Val Ser Gln Phe Lys Asp Ala Asp Leu
1               5                   10

<210> SEQ ID NO 36
<211> LENGTH: 14
<212> TYPE: PRT
<213> ORGANISM: Homo sapiens

<400> SEQUENCE: 36

Gly Ala Ser Pro Val Leu Ser Gln Gly Val Asp Pro Arg Ser
1               5                   10

<210> SEQ ID NO 37
<211> LENGTH: 14
<212> TYPE: PRT
<213> ORGANISM: Homo sapiens

<400> SEQUENCE: 37

Trp Glu Thr Pro Asp Leu Ser Gln Ala Glu Ile Glu Gln Lys
1               5                   10

```
<210> SEQ ID NO 38
<211> LENGTH: 14
<212> TYPE: PRT
<213> ORGANISM: Homo sapiens

<400> SEQUENCE: 38

Gln Pro Glu Pro Pro Val Ser Gln Ser Glu Ile Ser Glu Pro
  1               5                  10

<210> SEQ ID NO 39
<211> LENGTH: 14
<212> TYPE: PRT
<213> ORGANISM: Homo sapiens

<400> SEQUENCE: 39

Asp Leu Lys Leu Gly Val Ser Gln Gln Thr Ile Phe Ser Val
  1               5                  10

<210> SEQ ID NO 40
<211> LENGTH: 14
<212> TYPE: PRT
<213> ORGANISM: Homo sapiens

<400> SEQUENCE: 40

Phe Pro Ala Pro Ala Pro Ser Gln Ala Glu Lys Lys Ser Arg
  1               5                  10

<210> SEQ ID NO 41
<211> LENGTH: 14
<212> TYPE: PRT
<213> ORGANISM: Homo sapiens

<400> SEQUENCE: 41

Ile Val Pro Cys Thr Ile Ser Gln Leu Leu Ser Ala Thr Leu
  1               5                  10

<210> SEQ ID NO 42
<211> LENGTH: 14
<212> TYPE: PRT
<213> ORGANISM: Homo sapiens

<400> SEQUENCE: 42

Thr Gly Asn Val Glu Ile Ser Gln Val Thr Ile Val Gly Ile
  1               5                  10

<210> SEQ ID NO 43
<211> LENGTH: 9
<212> TYPE: PRT
<213> ORGANISM: Homo sapiens

<400> SEQUENCE: 43

Glu Leu Lys Pro Val Leu Ser Gln Gly
  1               5

<210> SEQ ID NO 44
<211> LENGTH: 14
<212> TYPE: PRT
<213> ORGANISM: Homo sapiens

<400> SEQUENCE: 44

Asp Pro Gly Ala Asp Leu Ser Gln Tyr Lys Met Asp Val Thr
  1               5                  10

<210> SEQ ID NO 45
<211> LENGTH: 14
```

```
<212> TYPE: PRT
<213> ORGANISM: Homo sapiens

<400> SEQUENCE: 45

Ser Pro Leu Ala Pro Val Ser Gln Gln Gly Trp Arg Ser Ile
 1               5                  10

<210> SEQ ID NO 46
<211> LENGTH: 36
<212> TYPE: DNA
<213> ORGANISM: Artificial Sequence
<220> FEATURE:
<223> OTHER INFORMATION: PCR primer

<400> SEQUENCE: 46
tccccaggaa ttcccggcca tcccagtaca ggatta                         36

<210> SEQ ID NO 47
<211> LENGTH: 36
<212> TYPE: DNA
<213> ORGANISM: Artificial Sequence
<220> FEATURE:
<223> OTHER INFORMATION: PCR primer

<400> SEQUENCE: 47
tgcggccgct cgagtttttt gttccatttt ggagac                         36

<210> SEQ ID NO 48
<211> LENGTH: 45
<212> TYPE: DNA
<213> ORGANISM: Artificial Sequence
<220> FEATURE:
<223> OTHER INFORMATION: PCR primer

<400> SEQUENCE: 48
gaatccctcg agcctaccgc catgtggaaa ctgctgcccg ccgcg               45

<210> SEQ ID NO 49
<211> LENGTH: 48
<212> TYPE: DNA
<213> ORGANISM: Artificial Sequence
<220> FEATURE:
<223> OTHER INFORMATION: PCR primer

<400> SEQUENCE: 49
gtcgacgagc ggccgccacc tcagggatct tctcctttt aaataagg             48
```